(12) United States Patent
Matsumoto et al.

(10) Patent No.: US 7,067,268 B1
(45) Date of Patent: Jun. 27, 2006

(54) ANTIBODIES AND UTILIZATION THEREOF

(75) Inventors: Hirokazu Matsumoto, Tsukuba (JP); Chieko Kitada, Sakai (JP); Shuji Hinuma, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/700,643

(22) PCT Filed: May 20, 1999

(86) PCT No.: PCT/JP99/02650

§ 371 (c)(1),
(2), (4) Date: Feb. 2, 2001

(87) PCT Pub. No.: WO99/60112

PCT Pub. Date: Nov. 25, 1999

(30) Foreign Application Priority Data

May 21, 1998 (JP) .......................................... 10-140293

(51) Int. Cl.
*G01N 33/53* (2006.01)

(52) U.S. Cl. ...................... 435/7.92; 435/7.1; 435/7.92; 435/7.93; 435/7.94; 435/7.95; 435/70.1; 435/70.2; 435/70.21; 436/518; 436/514; 436/547; 436/548; 530/380; 530/388.1; 530/388.2

(58) Field of Classification Search ................. 436/518, 436/547, 548, 514; 435/7.1, 7.92–7.95, 70.1, 435/70.2, 70.21; 530/380, 388.1, 388.2
See application file for complete search history.

(56) References Cited

FOREIGN PATENT DOCUMENTS

| | | |
|---|---|---|
| EP | 887417 A2 | 12/1998 |
| WO | WO 97/24436 | 7/1997 |
| WO | WO 98/49295 | 11/1998 |

OTHER PUBLICATIONS

Stongin., 1993. "Sensitivity, Specificity, and Predictive Value of Diagnostic Tests: Definitions and Clinical Applications", in Laboratory Diagnosis of Viral Infections, Lennette, E., ed. Marcel Dekker, Inc. New York, pp. 211–219.*

* cited by examiner

*Primary Examiner*—Bao-Thuy L. Nguyen
(74) *Attorney, Agent, or Firm*—Mark Chao; Elaine M. Ramesh

(57) ABSTRACT

The anti-19P2 ligand monoclonal antibodies of the invention (in particular P2L-1Ca) have very high binding ability and can neutralize the arachidonic acid metabolite releasing activity of the 19P2 ligand. Therefore, they can be used, among others, as diagnostic, prophylactic and/or therapeutic agents for various diseases caused by some or other abnormality in the pituitary function modulating activity (e.g. prolactin secretion promoting activity), central nervous system modulating activity and pancreatic function modulating activity, among others, supposedly possessed by the 19P2 ligand.

Figure 1:
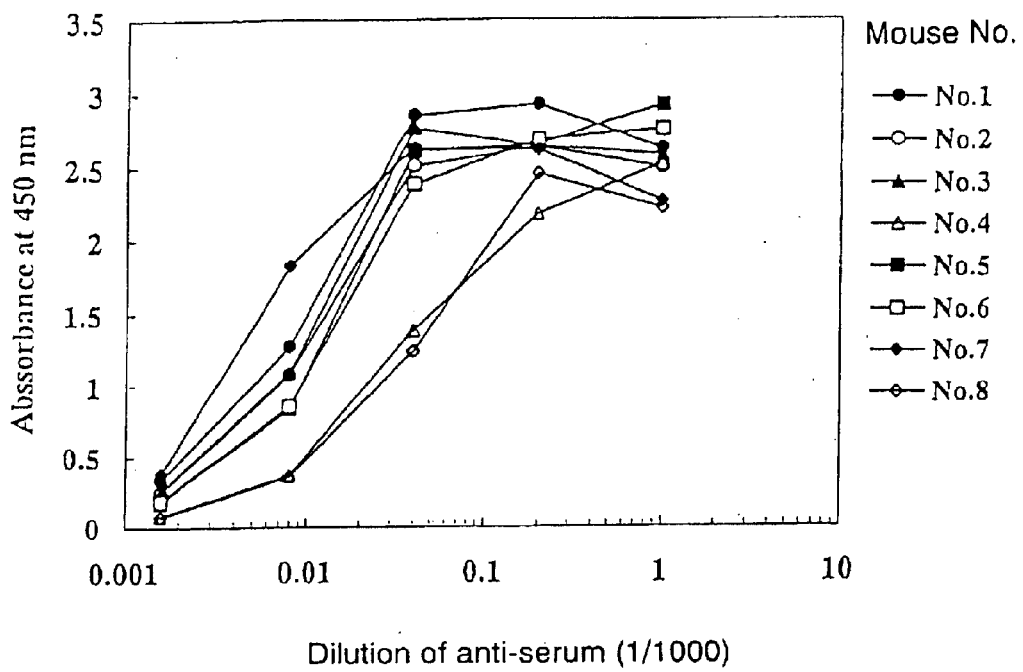

The immunoassay method using the monoclonal antibodies of the invention by the sandwich technique (in particular the sandwich technique using the monoclonal antibody and an antibody recognizing an intermediate portion of the 19P2 ligand) can assay the 19P2 ligand or a derivative thereof specifically and with high sensitivity. This assay method can be used in elucidating the physiological functions of the 19P2 ligand or a derivative thereof.

18 Claims, 11 Drawing Sheets a  Human 19P2 ligand derivative b  Bovine 19P2 ligand derivative a P2L-1Ta b P2L-3T a   P2L-1Ta b   P2L-3Ta

ANTIBODIES AND UTILIZATION THEREOF

This application is the National Stage of International Application No. PCT/JP99/02650, filed on May 20, 1999.

FIELD OF THE INVENTION

The present invention relates to a novel monoclonal antibody specifically binding to the 19P2 ligand or a derivative thereof. More particularly, the invention relates to an antibody useful for the development of a method of assaying the 19P2 ligand or a derivative thereof based on the antigen-antibody reaction and for the development of a diagnostic, prophylactic or therapeutic agent for diseases associated with the 19P2 ligand or a derivative thereof which utilizes the neutralizing activity thereof.

BACKGROUND OF THE INVENTION

The 19P2 ligand is a novel peptide found as a ligand to an orphan G protein-conjugated receptor (19P2). It occurs most abundantly in the brain (in particular hypothalamus) and its receptor, namely 19P2, is most abundantly localized in the pituitary gland. Therefore, it is thought to be one of novel hypothalamic hormones (pituitarotropic hormones). Its sequence suggests the occurrence of two 19P2 ligand species, namely (1) 19P2-L31 which is composed of 31 residues (a peptide composed of 31 amino acid residues) and (2) 19P2-L20 which begins with the 12th residue Thr (a peptide composed of 20 amino acid residues) (WO 97/24436). [Hereinafter, the 19P2 ligand composed of 31 amino acid residues is referred to also as "19P2 ligand (1–31) or 19P2-L31" and the 19P2 ligand composed of 20 amino acid residues is referred to also as "19P2 ligand (12–31) or 19P2-L20".]

The amino acid sequences of bovine, human and rat 19P2 ligand (1–31) species are shown below.

[Bovine 19P2 ligand (1–31)] (SEQ ID NO:1) H-Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$

[Human 19P2 ligand (1–31)] (SEQ ID NO:2) H-Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-Gly-Arg-Phe-NH$_2$

[Rat 19P2 ligand (1–31)] (SEQ ID NO:3) H-Ser-Arg-Ala-His-Gln-His-Ser-Met-Glu-Thr-Arg-Thr-Pro-Asp-Ile-Asn-Pro-Ala-Trp-Tyr-Thr-Gly-Arg-Gly-Ile-Arg-Pro-Val-Gly-Arg-Phe-NH$_2$ The amino acid sequences of bovine, human and rat 19P2 ligand (12–31) species are shown below.

[Bovine 19P2 ligand (12–31)] (SEQ ID NO:12) H-Thr-Pro-Asp-Ile-Asn-Pro-Ala-Trp-Tyr-Ala-Gly-Arg-Gly-Ile-Arg-Pro-Val-Gly-Arg-Phe-NH$_2$

[Human 19P2 ligand (12–31)] (SEQ ID NO:5) H-Thr-Pro-Asp-Ile-Asn-Pro-Ala-Trp-Tyr-Ala-Ser-Arg-Gly-Ile-Arg-Pro-Val-Gly-Arg-Phe-NH$_2$

[Rat 19P2 ligand (12–31)] (SEQ ID NO:13) H-Thr-Pro-Asp-Ile-Asn-Pro-Ala-Trp-Tyr-Thr-Gly-Arg-Gly-Ile-Arg-Pro-Val-Gly-Arg-Phe-NH2

Disorders of hypothalamic hormones, which are pituitary hormone regulating factors, are associated with various disease states. The 19P2 ligand, which is supposed to be one of hypothalamic hormones, is considered to have some function involving pituitary hormones. Its physiological functions, however, remain to be known yet in many respects. Therefore, development of a system capable of detecting and assaying the 19P2 ligand in an easy and simple manner and with high sensitivity has been earnestly awaited for elucidating the physiological activities of the 19P2 ligand.

DISCLOSURE OF THE INVENTION

It is an object of the present invention to provide a monoclonal antibody with which the 19P2 ligand or a derivative thereof can be specifically assayed with good sensitivity as well as a method of detecting or assaying the 19P2 ligand or a derivative thereof which utilizes said antibody.

The present inventors made intensive investigations to solve the above problems and, as a result, they created a plurality of monoclonal antibodies specifically recognizing different sites of the 19P2 ligand or a derivative thereof and developed a highly sensitive method of detecting or assaying the 19P2 ligand or a derivative thereof by using those antibodies and, after further investigations, they have now completed this invention.

Thus, the invention is concerned, among others, with an antibody (preferably a monoclonal antibody) specifically reacting with a C-terminal partial peptide of the 19P2 ligand or a derivative thereof, an antibody (preferably a monoclonal antibody) specifically reacting with an intermediate partial peptide of the 19P2 ligand or a derivative thereof, hybridoma cells producing such monoclonal antibodies, methods of producing such antibodies and such hybridoma cells, and an immunoassay method for assaying the 19P2 ligand or a derivative thereof by the competitive or sandwich technique which uses such antibodies.

More specifically, the present inventors prepared a plurality of monoclonal antibodies using [Cys$^{17}$]19P2 ligand (17–31) and [Cys$^{25}$]19P2 ligand (12–25) as immunogens and developed an immunoassay method capable of specifically detecting the 19P2 ligand or a derivative thereof with high sensitivity by using the above antibodies in a suitable combination. Thus, using the complex of bovine thyroglobulin (BTG) and [Cys$^{17}$]19P2 ligand (17–31) and that of BTG and [Cys$^{25}$]19P2 ligand (12–25) as immunogens, monoclonal antibodies recognizing a C-terminal site and an intermediate site of 19P2 ligand (1–31) or a derivative thereof, for example P2L-1Ca and P2L-1Ta, were established. It was revealed that when these two monoclonal antibodies are combinedly used in a competitive immunoassay using horseradish peroxidase (HRP)-labeled [Cys$^{17}$] 19P2 ligand (17–31) and HRP-labeled [Cys$^{25}$]19P2 ligand (12–25), there is provided a method of sandwich immunoassay which is exceptionally sensitive to 19P2-L31 and 19P2-L20. The present invention has thus made it possible to assay the 19P2 ligand simply, easily and with high sensitivity and, as such, is expected to be very useful in elucidating the physiological functions of the 19P2 ligand by monitoring its behavior or changes in level in biological components.

The present invention, therefore, relates to:
(1) A monoclonal antibody specifically reacting with a C-terminal partial peptide of the 19P2 ligand or a derivative thereof;
(2) A monoclonal antibody as defined above under (1) which is a mouse IgG;
(3) A monoclonal antibody as defined above under (2) which is referred to as P2L-1Ca or P2L-2Ca;
(4) A monoclonal antibody specifically reacting with an intermediate partial peptide of the 19P2 ligand or a derivative thereof;
(5) A monoclonal antibody as defined above under (4) which is a mouse IgG;

(6) A monoclonal antibody as defined above under (5) which is referred to as P2L-1Ta;
(7) A method of assaying the 19P2 ligand or a derivative thereof in a sample fluid which comprises using the monoclonal antibody defined above under (1) or (4);
(8) A method of assaying the 19P2 ligand or a derivative thereof in a sample fluid which comprises using the monoclonal antibodies defined above under (1) and (4);
(9) A hybridoma cell producing the monoclonal antibody defined above under (1) or (4);
and so forth.

The invention further relates to:
(10) A monoclonal antibody specifically reacting with a C-terminal partial peptide of the 19P2 ligand or a derivative thereof which is characterized in that it recognizes a partial peptide having the amino acid sequence of SEQ ID NO:7;
(11) A monoclonal antibody specifically reacting with an intermediate partial peptide of the 19P2 ligand or a derivative thereof which is characterized in that it recognizes a partial peptide having the amino acid sequence of SEQ ID NO:11;
(12) A method of assaying the 19P2 ligand or a derivative thereof in a sample fluid which comprises using the antibody defined above under (10) or (11):
(13) A method of assaying the 19P2 ligand or a derivative thereof in a sample fluid which comprises using the antibody defined above under (11) and the antibody defined above under (10);
(14) A method of assaying as defined above under (12) or (13) for use in the diagnosis of hyperprolactinemia;
and so forth.

As preferred embodiments of the monoclonal antibody defined above under (1), there may be mentioned, among others, the following:
(i) A monoclonal antibody as defined above under (10) wherein the 19P2 ligand is a peptide having the amino acid sequence of SEQ ID NO:1, SEQ ID NO:2, SEQ ID NO:3, SEQ ID NO:5 or SEQ ID NO:12;
(ii) A monoclonal antibody as defined above under (10) wherein the derivative of 19P2 ligand is (1) a peptide having the amino acid sequence of SEQ ID NO:7, (2) a peptide having the amino acid sequence covering from the 18th to the 31st amino acid residue of the amino acid sequence of SEQ ID NO:1, SEQ ID NO:2 or SEQ ID NO:3 and its C-terminal is an amide form; (3) a peptide having the amino acid sequence covering from the 8th to the 20th amino acid residue of the amino acid sequence of SEQ ID NO:5 or SEQ ID NO:12, or (4) a peptide having the amino acid sequence comprising the nine C-terminal residues of the amino acid sequence of one of SEQ ID NO:1 to SEQ ID NO:7, SEQ ID NO:10 and SEQ ID NO:11;
(iii) A monoclonal antibody as defined above under (10) wherein the C-terminal partial peptide of the 19P2 ligand or a derivative thereof has the amino acid sequence beginning with the 20th (from the N-terminal amino acid) residue of the 19P2 ligand;
(iv) A monoclonal antibody as defined above under (10) which does not recognize a partial peptide having the amino acid sequence of SEQ ID NO:9 wherein the C terminal is a carboxylic acid;
(v) A monoclonal antibody as defined above under (10) which recognizes a partial peptide having the amino acid sequence of SEQ ID NO:7 but does not recognize the amino acid sequence of SEQ ID NO:8;
(vi) A monoclonal antibody as defined above under (10) which recognizes a partial peptide having the amino acid sequence of SEQ ID NO:7 but does not recognize a peptide having the amino acid sequence of SEQ ID NO:10, which is lacking in the C-terminal Phe;
(vii) A monoclonal antibody as defined above under (10) referred to as P2L-1Ca or P2L-2Ca;
(viii) A monoclonal antibody as defined above under (10) which has neutralizing activity against those peptides which have the amino acid sequences of SEQ ID NO:1, SEQ ID NO:2, SEQ ID NO:3, SEQ ID NO:5 and SEQ ID NO:12, respectively; and so forth.

As preferred embodiments of the monoclonal antibody defined above under (4), there may be mentioned, among others, the following:
(i) A monoclonal antibody as defined above under (11) wherein the 19P2 ligand is a peptide having the amino acid sequence of SEQ ID NO:1, SEQ ID NO:2, SEQ ID NO:3, SEQ ID NO:5 or SEQ ID NO:12;
(ii) A monoclonal antibody as defined above under (11) wherein the derivative of the 19P2 ligand is (1) a peptide having the amino acid sequence covering from the 12th to 24th amino acid residue of the amino acid sequence of SEQ ID NO:1, (2) a peptide having the amino acid sequence covering from the 12th to the 24th amino acid residue of the amino acid sequence of SEQ ID NO:2 or (3) a peptide having the amino acid sequence covering from the 12th to the 24th amino acid residue of the amino acid sequence of SEQ ID NO:3;
(iii) A monoclonal antibody as defined above under (11) which does not recognize a peptide having the amino acid sequence of SEQ ID NO:4 or SEQ ID NO:6;
(iv) A monoclonal antibody as defined above under (11) referred to as P2L-1Ta or P2L-3Ta; and so forth.

As preferred hybridoma cells, there may be mentioned:
(i) Hybridoma cells producing the monoclonal antibody defined above under (10) or (11); and so forth.

As preferred embodiments of the assay method defined above under (12), there may be mentioned:
(i) A method of assaying the 19P2 ligand or a derivative thereof in a test fluid which comprises reacting the monoclonal antibody defined above under (10) or (11) competitively with the test fluid and a labeled form of the 19P2 ligand or a derivative thereof and determining the proportion of the labeled form 19P2 ligand or derivative thereof bound to said antibody; and so forth.

As preferred embodiments of the assay method defined above under (13), there may be mentioned;
(i) A method of assaying the 19P2 ligand or a derivative thereof in a test fluid which comprises reacting an antibody to the 19P2 ligand or a derivative thereof, which is immobilized on a carrier, and an antibody to the 19P2 ligand or a derivative thereof, which is labeled, with a test fluid and determining the activity of the labeling agent on the immobilizing carrier, wherein one of the antibody to the 19P2 ligand or a derivative thereof as immobilized on the carrier and the labeled antibody to the 19P2 ligand or a derivative thereof is the monoclonal antibody defined above under (10) and the other is the monoclonal antibody defined above under (11);
(ii) An assay method as described above under (i), wherein the monoclonal antibody defined above under (11) is the monoclonal antibody referred to as P2L-1Ta or P2L-3Ta;
(iii) An assay method as described above under (i), wherein one of the antibody to the 19P2 ligand as immobilized on the carrier and the labeled antibody to the 19P2 ligand is the monoclonal antibody referred to as P2L-1Ca or P2L-2Ca and the other is the monoclonal antibody referred to as P2L-1Ta or P2L-3Ta;

(iv) An assay method as described above under (i), wherein one of the antibody to the 19P2 ligand as immobilized on the carrier and the labeled antibody to the 19P2 ligand is the monoclonal antibody referred to as P2L-1Ca and the other is the monoclonal antibody referred to as P2L-2Ca, P2L-1Ta or P2L-3Ta and wherein the 19P2 ligand or a derivative thereof is a peptide having the amino acid sequence of SEQ ID NO:1, a peptide having the amino acid sequence of SEQ ID NO:2, a peptide having the amino acid sequence of SEQ ID NO:3 and/or a peptide having the amino acid sequence of SEQ ID NO:5;

(v) An assay method as described above under (i), wherein one of the antibody to the 19P2 ligand as immobilized on the carrier and the labeled antibody to the 19P2 ligand is the monoclonal antibody referred to as P2L-2Ca and the other is the monoclonal antibody referred to as P2L-1Ca, P2L-1Ta or P2L-3Ta and wherein the 19P2 ligand or a derivative thereof is a peptide having the amino acid sequence of SEQ ID NO:1, a peptide having the amino acid sequence of SEQ ID NO:2, a peptide having the amino acid sequence of SEQ ID NO:3, a peptide having the amino acid sequence of SEQ ID NO:12 and/or a peptide having the amino acid sequence of SEQ ID NO:5;

(vi) An assay method as described above under (i), wherein one of the antibody to the 19P2 ligand as immobilized on the carrier and the labeled antibody to the 19P2 ligand is the monoclonal antibody referred to as P2L-1Ta and the other is the monoclonal antibody referred to as P2L-1Ca or P2L-2Ca and wherein the 19P2 ligand or a derivative thereof is a peptide having the amino acid sequence of SEQ ID NO:1, a peptide having the amino acid sequence of SEQ ID NO:2, a peptide having the amino acid sequence of SEQ ID NO:3, a peptide having the amino acid sequence of SEQ ID NO:5 and/or a peptide having the amino acid sequence of SEQ ID NO:12; and so forth.

The 19P2 ligand in the present invention includes 19P2 ligand (1–31) composed of 31 amino acid residues and 19P2 ligand (12–31) composed of 20 amino acid residues. Thus, for instance, use is made of bovine 19P2 ligand (1–31) having the amino acid sequence of SEQ ID NO:1, human 19P2 ligand (1–31) having the amino acid sequence of SEQ ID NO:2, rat 19P2 ligand (1–31) having the amino acid sequence of SEQ ID NO:3, rat 19P2 ligand (12–31) having the amino acid sequence of SEQ ID NO:5, bovine 19P2 ligand (12–31) having the amino acid sequence of SEQ ID NO:12, etc.

As the derivative of the 19P2 ligand in the present invention, use is made of, among others, peptides derived from the 19P2 ligand by deletion of about 16 or 17 amino acid residues from the N terminus thereof, deletion of one C-terminal amino acid residue, substitution of D-alanine for L-glycine, substitution of a carboxylic acid for the C-terminal amide, addition of L-glycine and L-arginine to the C terminus, addition of L-cysteine, and/or acetylation of the N terminus, for instance. More specifically, use is made of (1) a peptide of SEQ ID NO:4 as derived from the amino acid sequence of 19P2-L31 by deletion of the 1st to 16th amino acid residues, (2) a peptide of SEQ ID NO:6 as resulting from addition of an acetyl group to the peptide of SEQ ID NO:4, (3) a peptide represented by H-Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-D-Ala-Arg-Phe-NH$_2$ derived from the amino acid sequence of 19P2-L31 by substitution of D-alanine from the 29th residue glycine, (4) a peptide of SEQ ID NO:8 as resulting from addition of L-glycine and L-arginine to the C terminus of 19P2-L31, (5) a peptide of SEQ ID NO:9 as resulting from conversion of the C-terminal amide of 19P2-L31 to carboxyl group, (6) a peptide of SEQ ID NO:10 as resulting from deletion of the 31st residue Phe from the amino acid sequence of 19P2-L31 and the like.

These 19P2 ligands or derivatives can be prepared (a) from mammals such as human, monkey, rat and mouse by a per se known method or (b) by chemical synthesis by a per se known method of peptide synthesis using a peptide synthesizer, for instance.

As the C-terminal partial peptide of the 19P2 ligand or a derivative thereof in the present invention, there may be mentioned a peptide having the amino acid sequence covering from the 18th to 31st residue of the amino acid sequence of SEQ ID NO:7 and having a cysteine residue added at the N terminus thereof.

As the antibody (preferably monoclonal antibody) specifically reacting with a C-terminal partial peptide of the 19P2 ligand or a derivative thereof in the present invention, use is made of antibodies recognizing the 19P2 ligand or a derivative thereof, for instance.

Among these antibodies, there may be mentioned, more specifically:

(i) Antibodies which recognize a partial peptide having the amino acid sequence of SEQ ID NO:7 (namely 19P2 ligand (18–31)) but do not recognize a partial peptide having the amino acid sequence of SEQ ID NO:11 (namely 19P2 ligand (12–24)); and (ii) Antibodies which recognize a partial peptide having the amino acid sequence of SEQ ID NO:7 (namely 19P2 ligand (18–31)) and further recognize a partial peptide having the amino acid sequence of SEQ ID NO:11 (namely 19P2 ligand (12–24)).

Among the antibodies mentioned above under (i) and (ii), those which are mouse IgG species, more preferably belonging to the subclass κ are preferably used.

Among the antibodies mentioned-above under (i), those antibodies which specifically recognize bovine 19P2 ligand (1–31) having the amino acid sequence of SEQ ID NO:1, human 19P2 ligand (1–31) having the amino acid sequence of SEQ ID NO:2, rat 19P2 ligand (1–31) having the amino acid sequence of SEQ ID NO:3, human 19P2 ligand (12–31) having the amino acid sequence of SEQ ID NO:5 and/or bovine 19P2 ligand (12–31) having the amino acid sequence of SEQ ID NO:12 are more preferred and, further, those antibodies which recognize human 19P2 ligand [D-Ala$^{29}$] (1–31) having the amino acid sequence H-Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-D-Ala-Arg-Phe-NH$_2$ but do not recognize human 19P2 ligand (1–30) having the amino acid sequence of SEQ ID NO:4, bovine 19P2 ligand (1–31)-OH having the amino acid sequence of SEQ ID NO:9, or bovine 19P2 ligand (1–31)-Gly-Ala-OH having the amino acid sequence of SEQ ID NO:8 are preferred.

Among the antibodies mentioned above under (ii), those antibodies which specifically recognize bovine 19P2 ligand (1–31) having the amino acid sequence of SEQ ID NO:1, human 19P2 ligand (1–31) having the amino acid sequence of SEQ ID NO:2, rat 19P2 ligand (1–31) having the amino acid sequence of SEQ ID NO:3 and/or human 19P2 ligand (12–31) having the amino acid sequence of SEQ ID NO:5 are preferred and, further, those antibodies which recognize human 19P2 ligand (1–30) having the amino acid sequence of SEQ ID NO:10 and bovine 19P2 ligand (1–31)-Gly-Ala-OH having the amino acid sequence of SEQ ID NO:8 are preferred.

A typical example of the above antibodies (i) is the monoclonal antibody referred to as P2L-1Ca and, as a typical example of the above antibodies (ii), there may be mentioned the monoclonal antibody referred to as P2L-2Ca.

In the next place, as the monoclonal antibodies specifically reacting with an intermediate partial peptide of the 19P2 ligand or a derivative thereof in the present invention, use is made of, for example, those monoclonal antibodies specifically reacting with the 19P2 ligand or a derivative thereof which are characterized in that they do not recognize the partial peptide having the amino acid sequence of SEQ ID NO:7 but recognize the partial peptide having the amino acid sequence of SEQ ID NO:11. Among these antibodies, those antibodies are preferred which particularly recognize bovine 19P2 ligand (1–31) having the amino acid sequence of SEQ ID NO:1, human 19P2 ligand (1–31) having the amino acid sequence of SEQ ID NO:2, rat 19P2 ligand (1–31) having the amino acid sequence of SEQ ID NO:3, human 19P2 ligand (12–31) having the amino acid sequence of SEQ ID NO:5, bovine 19P2 ligand (12–31) having the amino acid sequence of SEQ ID NO:12 and/or rat 19P2 ligand (12–31) having the amino acid sequence of SEQ ID NO:13 and those are preferred which do not recognize a peptide having the amino acid sequence derived from the amino acid sequence of SEQ ID NO:4 or SEQ ID NO:6 by deletion of the amino acid sequence covering from the 1st to the 16th residue. Among them, those which are mouse IgG species and, further, those belonging to the antibody subclass κ are preferably used. More specifically, such monoclonal antibodies as those referred to as P2L-1Ta, P2L-2Ta, P2L-3Ta, P2L-4Ta are used. Among these monoclonal antibodies, P2L-1Ta and the like are preferred.

In the following, the method of preparing antigens to be used in the production of the monoclonal antibodies of the invention and the method of preparing said monoclonal antibodies are described in detail.

(1) Antigen Preparation

The antigens to be used for the preparation of the antibodies of the invention may be of any kind and thus, for example, the 19P2 ligand, derivatives thereof and synthetic peptides having one or more antigenic determinants identical with those of the 19P2 ligand can be used (hereinafter, these are sometimes referred to merely as "19P2 ligand antigens").

As the 19P2 ligand or a derivative thereof, those species mentioned above and the like are used. These 19P2 ligand species or derivatives thereof can be prepared (a) from a tissue or cells of a mammal such as human, monkey, rat or mouse by a per se known method or a modification thereof or (b) by chemical synthesis by a per se known method of peptide synthesis using a peptide synthesizer or the like. Further, (c) such 19P2 ligand or a derivative thereof can be produced by cultivating a transformant harboring a DNA coding therefore.

(a) In the case of preparation from the mammalian tissue or cells, the tissue or cells are homogenized and then extracted with an acid, an alcohol or the like, and the antigen can be purified and isolated from the extract by a combination of such techniques as salting out, dialysis, gel filtration and chromatography, such as reversed phase chromatography, ion exchange chromatography, affinity chromatography, etc.

(b) In the case of chemical synthesis, the peptide to be synthesized may for example be one having the same structure as the 19P2 ligand antigen purified from a natural source as mentioned above or a peptide containing one or more amino acid sequences identical with the sequences consisting of 3 or more amino acid residues, preferably 6 or more residues, at arbitrary sites of the 19P2 ligand (1–31) or the like (hereinafter such peptide is referred to as "19P2 ligand-associated synthetic peptide" for short).

(c) In producing the 19P2 ligand or a derivative thereof using a transformant harboring an appropriate DNA, the DNA coding for the ligand or derivative can be constructed by a per se known method of cloning [for example, a method described in Molecular Cloning (2nd ed.; J. Sambrook et al., Cold Spring Harbor Lab. Press, 1989) etc.]. As said method of cloning, there may be mentioned, among others, (1) the method comprising isolating a transformant harboring a DNA coding for the desired peptide from a cDNA library by the technique of hybridization using a DNA probe or DNA primer designed based on the amino acid sequence of said peptide or (2) the method comprising obtaining a transformant harboring a DNA coding for the desired peptide by the technique of PCR using DNA primers designed based on the amino acid sequence of said peptide.

As mentioned above, the peptide as said antigen can be produced (1) by a conventional method of peptide synthesis or (2) by cleaving a peptide containing the peptide of the invention with an appropriate peptidase.

The method of peptide synthesis may be a solid phase method or a liquid phase method. Thus, the desired peptide can be produced by subjecting a partial peptide or an amino acid capable of constituting said peptide to condensation with the remaining portion thereof and deprotecting the condensation product if this had a protective group or groups. As methods of condensation and deprotection which are known in the art, there may be mentioned, for example, the methods described in the following monographs (1) and (2).

(1) M. Bodanszky and M. A. Ondetti, Peptide Synthesis, Interscience Publishers, New York (1966);

(2) Schroeder and Luebke, The Peptide, Academic Press, New York (1965).

After reaction, the peptide can be purified and isolated by a conventional method of purification, for example by a combination of solvent extraction, distillation, column chromatography, liquid chromatography, recrystallization, etc. The peptide obtained by the above method, when it is in the free form, can be converted to an appropriate salt by a method known in the art and, when it is obtained in the form of a salt, it can be converted to the free form by a conventional method.

In producing the peptide in an amide form, commercial resins for peptide synthesis suited for amide formation can be used. As such resins, there may be mentioned, among others, chloromethyl resins, hydroxymethyl resins, benzhydrylamine resins, aminomethyl resins, 4-benzyloxybenzyl alcohol resins, 4-methylbenzhydrylamine resins, PAM resins, 4-hydroxymethylmethylphenylacetamidomethyl resins, polyacrylamide resins, 4-(2',4'-dimethoxyphenyl-hydroxymethyl)phenoxy resins, 4-(2',4'-dimethoxyphenyl-Fmoc-aminoethyl)phenoxy resins and the like. Using such a resin, amino acids with the α-amino group and side chain function group thereof being appropriately protected are subjected to condensation on the resin according to the sequence of the desired peptide by various per se known methods of condensation. After the final reaction, the peptide is cut out from the resin and various protective groups are eliminated at the same time, whereby the desired peptide is obtained. Alternatively, when a chlorotrityl resin, oxime resin or 4-hydroxybenzoic acid type resin is used, it is also possible to obtain the desired peptide by cutting out the peptide in a partially protected form from the resin and further subjecting the same to deprotection in the conventional manner.

In effecting the condensation reactions of the protected amino acids, various activating reagents usable in peptide synthesis can be used and, among them, carbodiimides are preferred. As the carbodiimides, there may be mentioned DCC, N,N'-diisopropylcarbodiimide, N-ethyl-N'-(3-dimethylaminopropyl)carbodiimide, etc. For activation by such a reagent, the protected amino acid may be directly added to the resin together with a racemization inhibiting additive (e.g. HOBt, HOOBt), or the protected amino acid may be activated in advance as a symmetric anhydride or an ester of HOBt or HOOBt and then added to the resin. The solvent to be used in activating the protected amino acid or subjecting the same to condensation with the resin may be selected from among those solvents known to be usable in peptide condensation reactions. Thus, for example, use is made of acid amides such as N,N-dimethylformamide, N,N-dimethylacetamide and N-methylpyrrolidone, halogenated hydrocarbons such as methylene chloride and chloroform, alcohols such as trifluoroethanol, sulfoxides such as dimethyl sulfoxide, tertiary amines such as pyridine, ethers such as dioxane and tetrahydrofuran, nitriles such as acetonitrile and propionitrile, esters such as methyl acetate and ethyl acetate, and appropriate mixture of these. The reaction temperature is appropriately selected within the range known to be applicable to peptide bond formation reactions, generally within the range of about −20° C. to about 50° C. The activated amino acid derivative is generally used in about 1.5-fold to about 4-fold excess. When testing by the ninhydrin reaction indicates insufficient condensation, the condensation reaction can be repeated without deprotection to attain sufficient condensation. In cases where sufficient condensation cannot be attained upon repetition of the reaction, the unreacted amino acid may be inactivated by acetylation with acetic anhydride or acetylimidazole so that the succeeding reactions may not be affected.

As the protective group of the amino group of the raw material amino acid, there may be mentioned, for example, Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, etc. As the carboxy-protecting group, there may be mentioned, for example, $C_{1-6}$ alkyl groups, $C_{3-8}$ cycloalkyl groups, $C_{7-14}$ aralkyl groups and, further, 2-adamantyl, 4-nitrobenzyl, 4-methoxybenzyl, 4-chlorobenzyl, phenacyl as well as benzyloxycarbonylhydrazide, tert-butoxycarbonylhydrazide, tritylhyrazide, etc.

The hydroxy group of serine and of threonine can be protected by esterification or etherification. Suited as the group for this esterification are, for example, lower ($C_{1-6}$) alkanoyl groups such as acetyl, aroyl groups such as benzoyl, carbonic acid-derived groups such as benzyloxycarbonyl and ethoxycarbonyl, etc. Suited as the group for etherification are benzyl, tetrahydropyranyl, tert-butyl and the like.

As the protective group for the phenolic hydroxy group of tyrosine, there may be mentioned, for example, Bzl, $Cl_2$-Bzl, 2-nitrobenzyl, Br-Z, tert-butyl and the like.

As the imidazole-protecting group for histidine, there may be mentioned Tos, 4-methoxy-2,3,6-trimethylbenzenesulfonyl, DNP, Bom, Bum, Boc, Trt, Fmoc, etc.

As the activated form of the carboxyl group of each raw material, there may be mentioned, for example, the corresponding acid anhydride, azide and activated esters [esters with alcohols (e.g. pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt)]. The activated form of the amino group of each raw material, there may be mentioned the corresponding phosphoric amide.

As the method of eliminating the protective groups (deprotection), there may be mentioned, for example, catalytic reduction in a hydrogen atmosphere in the presence of a catalyst such as Pd black or Pd-on-carbon, treatment with an acid such as anhydrous hydrogen fluoride, methanesulfonic acid, trifluoromethanesulfonic acid, trifluoroacetic acid or a mixture of these, treatment with a base such as diisopropylethylamine, triethylamine, piperidine or piperazine, reduction with sodium in liquid ammonia, and so on. The deprotection by acid treatment is generally carried out at a temperature of −20° C. to 40° C. and it is effective in the acid treatment to add a cation trapping agent such as anisole, phenol, thioanisole, m-cresol, p-cresol, dimethyl sulfide, 1,4-butanedithiol or 1,2-ethanedithiol. The 2,4-dinitrophenyl group used as the imidazole-protecting group for histidine can be eliminated by treatment with thiophenol, and the formyl group used as the indole-protecting group for tryptophan can be eliminated by said acid treatment in the presence of 1,2-ethanedithiol, 1,4-butanedithiol or the like or by treatment with an alkali such as dilute sodium hydroxide or dilute ammonia.

The method for protection of the protective group for a functional group which is not to be involved in the reaction of the starting material as well as the method for elimination of the protective group and the method for activation of the functional group to be involved in the reaction can be appropriately selected from among the conventional methods and conventional groups.

According to an alternative method of obtaining the peptide in an amide form, the α-carboxyl group of the carboxyl-terminal amino acid is first amidated, the peptide chain is then extended on the amino group side to a desired chain length and, thereafter, only the protective group on the α-amino group at the N-terminus of the peptide chain is eliminated. Separately, the carboxyl-protecting group at the C-terminus alone of a peptide chain is eliminated to give a carboxyl-deprotected peptide (or amino acid). Both the peptides are then subjected to condensation in a mixed solvent such as mentioned above. The particulars of the condensation reaction are as mentioned above. The protected peptide obtained by the condensation is purified and all the protective groups are eliminated in the above manner, whereby the desired peptide can be obtained in a crude form. This crude peptide can be purified by utilizing various means of purification that are known in the art, and the main fraction is lyophilized to give the desired amide-form peptide.

For obtaining an ester form of the peptide, the α-carboxyl group of the carboxy-terminal amino acid is subjected to condensation with a desired alcohol to give the corresponding amino acid ester and then converted to the desired ester form peptide in the same manner as the amide form peptide.

The 19P2 ligand antigen is apt to aggregate and, therefore, an insolubilized form thereof may also be directly used for immunization. It is also possible to use a complex prepared by causing the 19P2 ligand antigen to bind to or be adsorbed on an appropriate carrier for immunization. The carrier and the mixing ratio between the carrier and the 19P2 ligand antigen (hapten) may be any carrier or mixing ratio provided that the 19P2 ligand antigen bound to or adsorbed on the carrier can cause efficient antibody production. A bound or adsorbed form of the antigen as obtained by using 0.1 to 100 parts by weight, per 1 part of the hapten, of a natural or synthetic macromolecular carrier commonly used in producing antibodies to hapten antigens can be used. Useful as the natural macromolecular carrier are serum albumin of a mammal such as cattle, rabbit or human, thyroglobulin of a mammal such as cattle or rabbit, hemoglobin of a mammal such as cattle, rabbit, human or sheep, keyhole limpet hemocyanin and the like. Usable as the synthetic macromolecular carrier are various latexes derived from polymers or copolymers, such as, for example, polyamino acids, polystyrenes, polyacrylics, polyvinyls and polypropylenes.

For coupling the hapten with the carrier, various condensing agents can be used. Preferably used are, for example, diazonium compounds such as bisdiazotized benzidine for crosslinking of tyrosine, histidine and tryptophan; dialdehyde compounds such as glutaraldehyde and diisocyanate compounds such as toluene-2,4-diisocyanate for amino group-amino group crosslinking; dimaleimide compounds such as N,N'-o-phenylenedimaleimide for thiol group-thiol group crosslinking: maleimide active ester compounds for amino group-thiol group crosslinking; and carbodiimide compounds for amino group-carboxyl group crosslinking. In amino group-amino group crosslinking, it is also possible to introduce a thiol group into one of the amino groups by reacting with a dithiopyridyl-containing active ester reagent (e.g. SPDP), followed by reduction, introduce a maleimido group into the other amino group by reacting with a maleimide active ester reagent and reacting both products with each other.

(2) Monoclonal Antibody Production

The 19P2 ligand antigen is administered, either as such or together with a carrier and/or diluent, to a warm-blooded animal at a site enabling antibody production by such a route of administration as intraperitoneal infusion, intravenous infusion or subcutaneous injection. On the occasion of such administration, Freund's complete adjuvant or Freund's incomplete adjuvant may be administered for increasing the antibody productivity. The administration is carried out generally about 2 to 10 times in total at intervals of 2 to 6 weeks. The warm-blooded animal includes, among others, monkey, rabbit, dog, guinea pig, mouse, rat, sheep, goat, chicken and the like. In monoclonal antibody production, the use of mice, rats or the like are preferred.

In monoclonal antibody production, individuals showing an antibody titer are selected from among warm-blooded animals, for example mice, immunized with the 19P2 ligand antigen and, 2 to 5 days after the final immunization, the spleen or lymphatic node is excised from each individual and antibody-producing cells contained therein are fused with myeloma cells, whereby anti-19P2 ligand monoclonal antibody-producing hybridomas can be prepared. The anti-19P2 ligand antibody titer in a serum sample is determined, for example, by reacting a labeled 19P2 ligand, which is to be mentioned later herein, with the antiserum and measuring the activity of the label bound to the antibody. The fusion procedure can be carried out by a method known in the art, for example the method of Koehler and Milstein [Nature, 256, 495 (1975)]. As the fusion promoter, there may be mentioned polyethylene glycol (PEG), Sendai virus and so on. PEG and the like are preferred, however. As the myeloma cells, there may be mentioned NS-1, P3U1, SP2/0, AP-1 and so forth. Among them, P3U1 and the like are preferred. A preferred ratio between the number of antibody-producing cells (splenocytes) and the number of myeloma cells is generally about 1:1 to 20:1, PEG (preferably PEG 1000 to PEG 6000) is added to a concentration of about 10 to 80%, and the cell fusion can be efficiently effected by incubating generally at 20 to 40° C., preferably 30 to 37° C., generally for 1 to 10 minutes.

For screening for anti-19P2 ligand antibody-producing hybridomas, various methods may be employed. Mention may be made of, for example, the method comprising adding the hybridoma culture supernatant to a solid phase (e.g. microplate) with the 19P2 ligand or a 19P2 ligand-related synthetic peptide adsorbed thereon either directly or together with a carrier, then adding an antiimmunoglobulin antibody (an anti-mouse immunoglobulin antibody when the cells used for cell fusion are murine cells) or protein A labeled with a radioactive substance or an enzyme and detecting the anti-19P2 ligand monoclonal antibody bound to the solid phase, and the method comprising adding hybridoma culture supernatant to a solid phase with an antiimmunoglobulin antibody or protein A adsorbed thereon, adding the 19P2 ligand labeled with a radioactive substance or an enzyme and detecting the anti-19P2 ligand monoclonal antibody bound to the solid phase. The anti-19P2 ligand monoclonal antibody screening and raising are generally carried out in a medium for animal cells (e.g. RPMI 1640) containing 10 to 20% fetal bovine serum and supplemented with HAT (hypoxanthine, aminopterine and thymidine). The hybridoma culture supernatant antibody titer can be measured in the same manner as the above-mentioned anti-19P2 ligand antibody titer determination in antisera.

The anti-19P2 ligand monoclonal antibody separation and purification are carried out by the same immunoglobulin separation and purification methods as in the separation and purification of ordinary polyclonal antibodies [e.g. salting out, alcohol precipitation, isoelectric precipitation, electrophoresis, adsorption/desorption using an ion exchanger (e.g. DEAE), ultracentrifugation, gel filtration, specific purification comprising collecting an antibody alone using an antibody-binding solid phase or an active adsorbent such as protein A or protein G and recovering the antibody by dissociating the binding].

The screening for a hybridoma producing an anti-19P2 ligand antibody reacting with a partial domain of the 19P2 ligand and a hybridoma producing an anti-19P2 ligand monoclonal antibody reacting with the 19P2 ligand but not reacting with a partial domain thereof can be carried out, for example, by determining the binding of a peptide corresponding to the partial domain to the antibody produced by the hybridoma.

(1) The monoclonal antibody referred to as P2L-1Ca, (2) the monoclonal antibody referred to as P2L-3Ca and (3) the monoclonal antibody referred to as P2L-3Ta and characterized by its specifically reacting with an intermediate partial peptide of the 19P2 ligand or a derivative thereof can respectively recognize the C-terminal and intermediate partial peptides of the 19P2 ligand and therefore can be used in assaying the 19P2 ligand in test fluids, in particular by sandwich immunoassay.

Thus, the present invention provides:

(1) A method of assaying the 19P2 ligand or a derivative thereof in a test fluid which comprises reacting an antibody of the invention to the 19P2 ligand or a derivative thereof competitively with the test fluid and a labeled form of the 19P2 ligand or a derivative thereof and determining the proportion of the labeled 19P2 ligand or a derivative thereof bound to said antibody:

(2) A method of assaying the 19P2 ligand or a derivative thereof in a test fluid which comprises reacting an antibody to the 19P2 ligand or a derivative thereof as immobilized on a carrier and a labeled antibody to the 19P2 ligand or a derivative thereof with the test fluid and determining the activity of the label on the insolubilizing carrier, wherein one of the antibody to the 19P2 ligand or a derivative thereof as immobilized on the carrier and the labeled antibody to the 19P2 ligand or the derivative thereof is an antibody characterized by its specifically reacting with a C-terminal partial peptide of the 19P2 ligand or the derivative thereof and the other is an antibody recognizing an intermediate part of the 19P2 ligand or the derivative thereof, such as a partial peptide having the amino acid sequence of SEQ ID NO:11 (namely 19P2 ligand (12–24)); and so on.

More specifically, the antibody characterized by its specifically reacting with a C-terminal partial peptide of the 19P2 ligand or a derivative thereof is the monoclonal antibody referred to as P2L-1Ca or P2L-2Ca and the antibody recognizing an intermediate part of the 19P2 ligand or a derivative thereof, such as a partial peptide having the amino acid sequence of SEQ ID NO:11 (namely 19P2 ligand (12–24)), is the monoclonal antibody referred to as P2L-1Ta or P2L-3Ta.

Preferred as the above assay method (2) are, in particular:
(1) A method of assaying as mentioned above, wherein one of the antibody to the 19P2 ligand as immobilized on a carrier and the labeled antibody to the 19P2 ligand or a derivative thereof is the monoclonal antibody referred to as P2L-1Ca and the other is the monoclonal antibody referred to as P2L-1Ta or P2L-3Ta and the 19P2 ligand is a peptide having the amino acid sequence of SEQ ID NO:1, SEQ ID NO:2, SEQ ID NO:3, SEQ ID NO:5 or SEQ ID NO:12;
(2) A method of assaying as mentioned above, wherein one of the antibody to the 19P2 ligand as immobilized on a carrier and the labeled antibody to the 19P2 ligand or a derivative thereof is the monoclonal antibody referred to as P2L-2Ca and the other is the monoclonal antibody referred to as P2L-1Ta or P2L-3Ta and the 19P2 ligand is a peptide having the amino acid sequence of SEQ ID NO:1, SEQ ID NO:2, SEQ ID NO:3, SEQ ID NO:5 or SEQ ID NO:12; and so forth.

In the following, the method of assaying (immunoassaying) the 19P2 ligand or a derivative thereof (hereinafter collectively referred to as "19P2 ligand") according to the invention is described in more detail.

The antibody of the invention can recognize 19P2 ligand and therefore can assay 19P2 ligand or detect it by tissue staining, for instance. For these purposes, the antibody molecule may be used as it is or the F(ab')$_2$, Fab' or Fab fraction of the antibody molecule, for instance, may be used. The assay method using the antibody of the invention is not particularly restricted but includes all techniques by which the amount of an antibody, antigen or antibody-antigen complex which corresponds to the amount of an antigen (e.g. amount of 19P2 ligand) in a test fluid is detected by chemical or physical means and said amount is calculated from a reference curve constructed by using standard solutions each containing a known amount of the antigen. For example, nephelometric, competitive, immunometric, sandwich and other techniques are preferably used. From the viewpoint of sensitivity and specificity, the sandwich technique to be mentioned later herein is particularly preferred.

The label to be used in assay methods using a labeled substance may be a radioactive isotope, an enzyme, a fluorescent substance, a chemiluminescent substance or the like. Preferred as the radioactive isotope are, for example, $^{125}$I, $^{131}$I, $^{3}$H and $^{14}$C, among others. Preferred as the enzyme are those which are stable and are high in specific activity, such as β-galactosidase, β-glucosidase, alkaline phosphatase, peroxidase and malate dehydrogenase. As the fluorescent substance, there may be mentioned, among others, fluorescamine and fluorescein isothiocyanate and, as the chemiluminescent substance, luminol, luminol derivatives, luciferin and lucigenin, among others. Further, the biotin-avidin system may also be used for binding an antibody or 19P2 ligand to the label.

In antigen or antibody immobilization, physical adsorption may be utilized or a chemical binding method generally used in insolubilizing or immobilizing proteins, enzymes and so on may be used. As the carrier, there may be mentioned, among others, insoluble polysaccharides such as agarose, dextran and cellulose, synthetic resins such as polystyrene, polyacrylamide and silicones, and glass.

According to the sandwich technique, the test fluid is reacted with an immobilized anti-19P2 ligand antibody (primary reaction) and, after further reacting with a labeled anti-19P2 ligand antibody (secondary reaction), the activity of the label on the immobilizing carrier was assayed, whereby the amount of 19P2 ligand in the test fluid can be determined. The primary and secondary reactions may be carried out simultaneously or at a certain time interval. The label and the method of immobilization are the same as those mentioned above. In immunoassaying by the sandwich technique, the antibody to be used as a solid phase antibody or a labeled antibody need not comprise one single species but a mixture of two or more antibody species may be used for improving the sensitivity of the assay.

In assaying 19P2 ligand by the sandwich technique according to the invention, it is desirable that the anti-19P2 ligand antibody for the primary reaction and that for the secondary reaction differ in 19P2 ligand binding site. For example, when the antibody used for the primary reaction recognizes a C-terminal partial peptide of 19P2 ligand, the antibody to be used in the secondary reaction is preferably an antibody recognizing a site other than the C-terminal partial peptide (namely an N-terminal or intermediate partial peptide).

Specifically, the monoclonal antibody specifically reacting with a C-terminal partial peptide of 19P2 ligand, which is to be used in sandwich immunoassay according to the invention, is, for example, a monoclonal antibody produced by using [Cys$^{17}$]-human 19P2 ligand (17–31) as the immunogen. The present inventors have established eight hybridoma lines producing such an antibody. Among them, the antibody produced by the hybridoma P2L-1C reacted with human, bovine and rat 19P2 ligand (1–31) in competitive enzyme immunoassay using peroxidase-labeled 19P2 ligand (17–31), as mentioned later herein (antigen concentration give B/B0=0.5: 3 nM, 1.1 ng/well). Further, it has been unexpectedly found that when they are used in a sandwich assay in combination with the monoclonal antibody produced by using [Cys$^{25}$]-19P2 ligand (12–25) as the immunogen, as mentioned later herein, and recognizing an intermediate partial peptide of 19P2 ligand, in particular P2L-1Ta, 19P2 ligand can be assayed with higher sensitivity (detection sensitivity: 0.1 fmol/well). Thus, it is not always necessary that the monoclonal antibody specifically reacting with a C-terminal partial peptide of 19P2 ligand which is suited for use in the sandwich immunoassay method according to the invention have high affinity for 19P2 ligand (1–31). Thus, P2L-1Ta, for instance, is favorably used as such antibody.

On the other hand, suited for use as the monoclonal antibody recognizing an intermediate partial peptide of 19P2 ligand and to be used in sandwich immunoassay according to the invention are antibodies produced by using [Cys$^{25}$]-19P2 ligand (12–25) as the immunogen. The present inventors have produced 12 hybridoma species producing such antibodies (Table 2). Upon examination of these antibodies for reactivity with 19P2 ligand (12–25) by the competitive method using peroxidase-labeled 19P2 ligand (12–25), as mentioned later herein, it was revealed that four antibodies show good reactivity with 19P2 ligand (12–25) (antigen concentration giving B/B0=0.5: 1 to 4 nM, 0.9 to 1.6 ng/well) and P2L-1Ta and P2L-3Ta have good reactivity with 19P2 ligand (1–31). It was revealed that, among them, P2L-1Ta, in particular, gives a very high sensitivity sandwich assay method. P2L-1Ta showed the same level of reactivity with 19P2 ligand (12–31) as well. Thus, while, according to the invention, several monoclonal antibodies to 19P2 ligand (12–24) have been provided as antibodies recognizing an intermediate partial peptide of 19P2 ligand which are suited for use in the sandwich method, P2L-1Ta is particularly suited for use.

The monoclonal antibodies of the invention can be used also in assay systems other than the sandwich method, for example in competitive, immunometric, nephelometric and like methods. In the competitive method, the antigen in the test fluid and a labeled form of the antigen are competitively reacted with an antibody, the unreacted labeled antigen (F) and the antibody-bound labeled antigen (B) are separated from each other (B/F separation) and the label of either B or F is quantitated to thereby assay the antigen in the test fluid. This reaction method includes the liquid phase method in which a soluble antigen is used as the antigen and, in B/F separation, polyethylene glycol or a second antibody to the above antibody is used and the solid phase method using a solid phase antibody as the first antibody or using a soluble antibody as the first antibody and a solid phase antibody as the second antibody, among others.

In the immunometric method, the antigen in the test fluid and the antigen on a solid phase are competitively reacted with a known amount of a labeled form of the antibody and then the solid phase and liquid phase are separated from each other, or the antigen in the test fluid is reacted with an excessive amount of a labeled form of the antibody, then the antigen on a solid phase is added to thereby bind the unreacted labeled antibody to the solid phase, and the solid phase and liquid phase are separated from each other. Then, the label in either of the phases is assayed and the antigen titer of the test fluid is determined accordingly.

In nephelometry, the amount of an insoluble precipitate resulting from the antigen-antibody reaction in a gel or solution is measured. Even when the antigen amount in the test fluid is slight and the precipitate is obtained only in a small amount, laser nephelometry utilizing the scattering of laser beams is favorably used.

In applying these respective immunological assay methods to the method of the invention, it is not necessary to establish particular conditions or carry out particular operations. An appropriate 19P2 ligand assaying system can be constructed by giving technical considerations, which are obvious to those skilled in the art, to the conditions and operations which are conventional in the respective methods. For details of these conventional technical means, reference may be made to the review articles and monographs [cf. e.g. Hiroshi Irie (ed.), "Rajioimunoassei (Radioimmunoassay)" (Kodansha, 1974); Hiroshi Irie (ed.), "Zoku Rajioimunoassei (Radioimmunoassay, Supplemental)" (Kodansha, 1979); Eiji Ishikawa et al. (eds.), "Koso Men'eki Sokuteiho (Enzyme Immunoassay)" (Igaku Shoin, 1978); Eiji Ishikawa et al. (eds.), "Koso Men'eki Sokuteiho (Enzyme Immunoassay)" (2nd ed.) (Igaku Shoin, 1982); Eiji Ishikawa et al. (eds.), "Koso Men'eki Sokuteiho (Enzyme Immunoassay)" (3rd ed.) (Igaku Shoin, 1987); "Methods In Enzymology", vol. 70 (Immunochemical Techniques (Part A)), ibid., vol. 73 (Immunochemical Techniques (Part B)), ibid., vol. 74 (Immunochemical Techniques (Part C)), ibid., vol. 84 (Immunochemical Techniques (Part D: Selected Immunoassays), ibid., vol. 92 (Immunochemical Techniques (Part E: Monoclonal Antibodies and General Immunoassay Methods)), ibid., vol. 121 (Immunochemical Techniques (Part I: Hybridoma Technology and Monoclonal Antibodies)) (Academic Press); etc.]. Thus, in constructing a 19P2 ligand assaying system for the sandwich immunoassay method according to the invention, the method of system construction is not limited to the examples mentioned later herein.

As mentioned above, the antibodies of the invention can assay the 19P2 ligand or a derivative thereof with good sensitivity and therefore are useful, among others, in elucidating the physiological functions of the 19P2 ligand and diagnosing diseases in which the 19P2 ligand is involved.

In the present specification, when amino acids and others are symbolized, the abbreviations or symbols used are those recommended by the IUPAC-IUB Commission on Biochemical Nomenclature or those conventionally used in the relevant field of art. The following are examples thereof. In cases where optical isomers are possible for an amino acid mentioned, the amino acid is in the L-form, unless otherwise specified.

PAM: Phenylacetamidomethyl;
Boc: tert-Butoxycarbonyl;
Fmoc: 9-Fluorenylmethyloxycarbonyl;
Cl-Z: 2-Chlorobenzyloxycarbonyl;
Br-Z: 2-Bromobenzyloxycarbonyl;
Bzl: Benzyl;
$Cl_2$-Bzl: 2,6-Dichlorobenzyl;
OcHex: Cyclohexyl ester;
OBzl: Benzyl ester;
Tos: p-Toluenesulfonyl;
HONB: N-Hydroxy-5-norbornene-2,3-dicarboxyimide;
HOBt: 1-Hydroxybenzotriazole;
HOOBt: 3-Hydroxy-3,4-dihydro-4-oxo-1,2,3-benzotriazine;
MeBzl: 4-Methylbenzyl;
Bom: Benzyloxymethyl;
Bum: tert-Butoxymethyl;
Trt: Trityl;
DNP: Dinitrophenyl;
TFA: Trilfuoroacetic acid;
DMF: N,N-Dimethylformamide;
DCM: Dichloromethane;
DCC: N,N'-Dicyclohexylcarbodiimide
BHA: Benzhydrylamine;
pMBHA: p-Methylbenzhydrylamine;
CHO: Formyl;
DIEA: Diisopropylethylamine;
2-Ac-human 19P2 ligand:
  [AcPro17,Tyr(Ac)20]human 19P2 ligand (17–31);
Gly: Glycine;
Ala: Alanine;
Val: Valine;
Leu: Leucine;
Ile: Isoleucine;
Ser: Serine;
Thr: Threonine;
Cys: Cysteine;
Met: Methionine;
Glu: Glutamic acid;
Asp: Aspartic acid;
Lys: Lysine;

Arg: Arginine;
His: Histidine;
Phe: Phenylalanine;
Tyr: Tyrosine;
Trp: Tryptophan;
Pro: Proline;
Asn: Asparagine;
Gln: Glutamine.

The sequence identifier numbers used in this specification respectively represent the amino acid sequences of the following peptides.

[SEQ ID NO:1] Bovine 19P2 ligand (1–31) H-Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$

[SEQ ID NO:2] Human 19P2 ligand (1–31) H-Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-Gly-Arg-Phe-NH$_2$

[SEQ ID NO:3] Rat 19P2 ligand (1–31) H-Ser-Arg-Ala-His-Gln-His-Ser-Met-Glu-Thr-Arg-Thr-Pro-Asp-Ile-Asn-Pro-Ala-Trp-Tyr-Thr-Gly-Arg-Gly-Ile-Arg-Pro-Val-Gly-Arg-Phe-NH$_2$

[SEQ ID NO:4] Human 19P2 ligand (17–31) H-Pro-Ala-Trp-Tyr-Ala-Ser-Arg-Gly-Ile-Arg-Pro-Val-Gly-Arg-Phe-NH$_2$

[SEQ ID NO:5] Human 19P2 ligand (12–31) H-Thr-Pro-Asp-Ile-Asn-Pro-Ala-Trp-Tyr-Ala-Ser-Arg-Gly-Ile-Arg-Pro-Val-Gly-Arg-Phe-NH$_2$

[SEQ ID NO:6] Diacetylated human 19P2 ligand (17–31) Ac-Pro-Ala-Trp-Tyr(Ac)-Ala-Ser-Arg-Gly-Ile-Arg-Pro-Val-Gly-Arg-Phe-NH$_2$

[SEQ ID NO:7] [Cys$^{17}$]-Human 19P2 ligand (17–31) H-Cys-Ala-Trp-Tyr-Ala-Ser-Arg-Gly-Ile-Arg-Pro-Val-Gly-Arg-Phe-NH$_2$

[SEQ ID NO:8] Bovine 19P2 ligand (1–31) Gly-Arg-OH H-Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-Gly-Arg-OH

[SEQ ID NO:9] Bovine 19P2 ligand (1–31)-OH H-Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-OH

[SEQ ID NO:10] Human 19P2 ligand (1–30) H-Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-Gly-Arg-NH$_2$

[SEQ ID NO:11] [Cys$^{25}$]-Human 19P2 ligand (12–25) H-Thr-Pro-Asp-Ile-Asn-Pro-Ala-Trp-Tyr-Ala-Ser-Arg-Gly-Cys-NH$_2$

[SEQ ID NO:12] Bovine 19P2 ligand (12–31) H-Thr-Pro-Asp-Ile-Asn-Pro-Ala-Trp-Tyr-Ala-Gly-Arg-Gly-Ile-Arg-Pro-Val-Gly-Arg-Phe-NH$_2$

[SEQ ID NO:13] Rat 19P2 ligand (12–31) H-Thr-Pro-Asp-Ile-Asn-Pro-Ala-Trp-Tyr-Thr-Gly-Arg-Gly-Ile-Arg-Pro-Val-Gly-Arg-Phe-NH$_2$ Among the hybridoma cell lines producing the anti-19P2 ligand antibodies as obtained in the examples mentioned later herein, P2L-1C and P2L-1T have been deposited with the Ministry of International Trade and Industry National Institute of Bioscience and Human Technology (NIBH; 1-3, Higashi 1-chome Tsukuba-shi, Ibaraki-ken, 305-8566 JAPAN) under the terms of the Budapest Treaty for the deposit of microorganisms for patent purposes, as of Mar. 18, 1998 under the respective accession numbers shown below:

| Hybridoma cell line | FERM-BF (NIBH) |
|---|---|
| P2L-1C | 6299 |
| P2L-1T | 6300 |

The antibody obtained from each hybridoma cell line is designated by the cell line name followed by the suffix a.

The following examples, inclusive of experimental examples, illustrate the present invention in further detail. These are, however, by no means limitative of the scope of the invention.

EXAMPLE 1

Antigen Preparation
(1) Production of 19P2 Ligand

EXPERIMENTAL EXAMPLE 1

Production of Bovine 19P2 Ligand (1–31)
1) Synthesis of Ser(Bzl)-Arg(Tos)-Ala-His(Bom)-Gln-His(Bom)-Ser(Bzl)-Met-Glu(OcHex)-Ile-Arg(Tos)-Thr(Bzl)-Pro-Asp(OcHex)-Ile-Asn-Pro-Ala-Trp(CHO)-Tyr(Br-Z)-Ala-Gly-Arg(Tos)-Gly-Ile-Arg(Tos)-Pro-Val-Gly-Arg(TOs)-Phe-pMBHA-resin A commercial p-methylBHA resin (product of Applied Biosystems, currently Perkin Elmer) (0.71 g, 0.5 mmole) was placed in the reactor of a peptide synthesizer (Applied Biosystems model 430A) and swollen with dichloromethane (DCM) and, then, the first amino acid Boc-Phe activated by the HOBt/DCC method was introduced into the p-methylBHA resin. The resin was treated with 50 TFA/DCM to thereby eliminate the Boc group and liberate the amino group, followed by neutralization with diisopropylethylamine (DIEA). This amino group was condensed with the next amino acid Boc-Arg(Tos) by the HOBt/DCC method. The presence or absence of the unreacted amino group was checked by the ninhydrin test and, after confirmation of the completion of the reaction, Boc-Gly, Boc-Val, Boc-Pro, Boc-Arg(Tos), Boc-Ile, Boc-Gly, Boc-Arg(Tos), Boc-Gly, Boc-Ala and Boc-Tyr(Br-Z) were subjected to condensation in the same manner. The ninhydrin test indicated insufficient condensation between Boc-Ala and Boc-Tyr(Br-Z) and; therefore, this condensation reaction was carried out again to complete the whole reaction. The resin was dried, half of the resin was taken out and the remaining half was subjected to condensation with Boc-Trp(CHO), Boc-Ala, Boc-Pro, Boc-Asn, Boc-Ile, Boc-Asp(OcHex), Boc-Pro, Boc-Thr(Bzl), Boc-Arg(Tos), Boc-Ile, Boc-Glu(OcHex), Boc-Met, Boc-Ser(Bzl), Boc-His(Bom), Boc-Gln, Boc-His(Bom), Boc-Ala, Boc-Arg(Tos) and Boc-Ser(Bzl) in the same manner while, if necessary, repeating the condensation procedure until sufficient condensation was confirmed by the ninhydrin test. The resin with the whole amino acid sequence introduced therein was treated with 50% trifluoroacetic acid (TFA)/DCM to thereby eliminate Boc groups on the resin and then dried to give 1.28 g of the title peptide resin.

2) Synthesis of Ser-Arg-Ala-His-Gln-His-Ser-Met-Glu-Ile-Arg-Thr-Pro-Asp-Ile-Asn-Pro-Ala-Trp-Tyr-Ala-Gly-Arg-Gly-Ile-Arg-Pro-Val-Gly-Arg-Phe-NH$_2$ The resin obtained as described above under 1) was treated with 3.8 g of p-cresol, 1 ml of 1,4-butanedithiol and 10 ml of hydrogen fluoride in a Teflon-made hydrogen fluoride reaction apparatus at 0° C. for 60 hours. The hydrogen fluoride and 1,4-butanedithiol (1 ml) were distilled off under reduced pressure, 100 ml of diethyl ether was added to the residue, the mixture was stirred and then filtered through a glass filter, and the solid was dried. This was suspended in 50 ml of 50% aqueous acetic acid, the suspension was stirred, and the peptide thus extracted was separated from the resin, concentrated to about 5 ml under reduced pressure and applied to a Sephadex G-25 column (2×90 cm), followed by development with 50% aqueous acetic acid. The fractions from 114 ml to 181 ml were collected and lyophilized to give 290 mg of a white powder. This was applied to a reversed phase column packed with LiChroprep RP-18 (product of Merck) and gradient elution was carried out using 0.1% aqueous TFA and 0.1% TFA-containing aqueous solution of 30% acetonitrile. This purification procedure by gradient elution was repeated, and the eluate fractions obtained at an acetonitrile concentration of about 25% were combined and lyophilized to give 71 mg of a white powder.

Mass analysis $(M+H)^+$: 3574.645 (calculated value 3574.847);

HPLC elution time: 18.2 minutes;

Column Conditions:

Column: Wakosil 5C18 (4.6×100 mm)

Eluent: Solution A (0.1% TFA-water)

Solution B (0.1% TFA-containing 50% acetonitrile-water)

Linear concentration gradient elution from solution A to solution B (25 minutes)

Flow rate: 1.0 ml/minute.

EXPERIMENTAL EXAMPLE 2

Production of Human 19P2 Ligand (1–31)

Following the same procedure as in Experimental Example 1, the p-methylBHA resin was condensed in sequence with Boc-Phe, Boc-Arg(Tos), Boc-Gly, Boc-Val, Boc-Pro, Boc-Arg(Tos), Boc-Ile, Boc-Gly, Boc-Arg(Tos), Boc-Ser(Bzl), Boc-Ala, Boc-Tyr(Br-Z), Boc-Trp(CHO), Boc-Ala, Boc-Pro, Boc-Asn, Boc-Ile, Boc-Asp(OcHex), Boc-Pro, Boc-Thr(Bzl), Boc-Arg(Tos), Boc-Ile, Boc-Glu (OcHex), Boc-Met, Boc-Ser(Bzl), Boc-His(Bom), Boc-Arg (Tos), Boc-His(Bom), Boc-Thr(Bzl), Boc-Arg(Tos) and Boc-Ser(Bzl) while, if necessary, repeating the condensation procedure until sufficient condensation was confirmed by the ninhydrin test. The resin with the whole amino acid sequence introduced therein was treated with 50% TFA/DCM to thereby eliminate Boc groups on the resin and the resin was then dried, whereby the desired peptide resin was synthesized. This resin was treated with hydrogen fluoride in the same manner as in Experimental Example 1 and purified by chromatography in the same manner to give the desired peptide.

Mass analysis $(M+H)^+$: 3662.884 (calculated value 3662.905);

HPLC elution time: 17.2 minutes;

Column Conditions:

Column: Wakosil 5C18 (4.6×100 mm)

Eluent: Solution A (0.1% TFA-water)

Solution B (0.1% TFA-containing 50% acetonitrile-water)

Linear concentration gradient elution from solution A to solution B (25 minutes)

Flow rate: 1.0 ml/minute.

EXPERIMENTAL EXAMPLE 3

Production of Rat 19P2 Ligand (1–31)

The synthetic procedure of Experimental Example 1 was followed using Boc-Thr(Bzl) in lieu of Boc-Ala in the first synthetic run and of Boc-Ile in the second run. The resin with the whole amino acid sequence introduced therein was treated with 50% TFA/DCM to thereby eliminate Boc groups on the resin and the resin was then dried to give the desired peptide resin. This resin was treated and the peptide purified in the same manner as in Experimental Example 1 to give Ser-Arg-Ala-His-Gln-His-Ser-Met-Glu-Thr-Arg-Thr-Pro-Asp-Ile-Asn-Pro-Ala-Trp-Tyr-Thr-Gly-Arg-Gly-Ile-Arg-Pro-Val-Gly-Arg-Phe-$NH_2$ as a white powder.

Mass analysis $(M+H)^+$: 3622.547 (calculated value 3622.826);

HPLC elution time: 17.4 minutes;

Column Conditions:

Column: Wakosil 5C18 (4.6×100 mm)].

Eluent: Solution A (0.1% TFA-water)

Solution B (0.1% TFA-containing 50% acetonitrile-water)

Linear concentration gradient elution from solution A to solution B (25 minutes)

Flow rate: 1.0 ml/minute.

EXPERIMENTAL EXAMPLE 4

Production of Human 19P2 Ligand (17–31)

The resin obtained after condensation of Boc-Tyr(Br-Z) in Experimental Example 2 was further condensed with Boc-Trp(CHO), Boc-Ala and Boc-Pro to give Boc-Pro-Ala-Trp (CHO)-Tyr(Br-Z)-Ala-Gly-Arg(Tos)-Gly-Ile-Arg(Tos)-Pro-Val-Gly-Arg(Tos)-Phe-pMBHA resin. This resin was subjected to the hydrogen fluoride treatment and purification by column chromatography in the same manner as in Experimental Example 1–2) to give 70 mg of a white powder.

Mass analysis $(M+H)^+$: 1731.9 (calculated value 1732.0);

HPLC elution time: 16.1 minutes;

Column Conditions:

Column: Wakosil 5C18 (4.6×100 mm)

Eluent: Solution A (0.1% TFA-water)

Solution B (0.1% TFA-containing 50% acetonitrile-water)

Linear concentration gradient elution from solution A to solution B (15 minutes)

Flow rate: 1.0 ml/minute.

EXPERIMENTAL EXAMPLE 5

Production of Human 19P2 Ligand (12–31)

The resin obtained after condensation of Boc-Pro in Experimental Example 4 was further condensed with Boc-Asn, Boc-Ile, Boc-Asp(OcHex), Boc-Pro and Boc-Thr(Bzl), to give Boc-Thr(Bzl)-Pro-Asp(OcHex)-Ile-Asn-Pro-Ala-Trp(CHO)-Tyr(Br-Z)-Ala-Gly-Arg(Tos)-Gly-Ile-Arg(Tos)-Pro-Val-Gly-Arg(Tos)-Phe-pMBHA resin. This resin was subjected to the hydrogen fluoride treatment and purification by column chromatography in the same manner as in Experimental Example 4 to give 60 mg of a white powder.

Mass analysis $(M+H)^+$: 2272.1260 (calculated value 2272.2100);

HPLC elution time: 16.8 minutes;

Column Conditions:

Column: Wakosil 5C18 (4.6×100 mm)

Eluent: Solution A (0.1% TFA-water)

Solution B (0.1% TFA-containing 50% acetonitrile-water)

Linear concentration gradient elution from solution A to solution B (25 minutes)
Flow rate: 1.0 ml/minute.

EXPERIMENTAL EXAMPLE 6

Production of Diacetylated Human 19P2 Ligand (17–31)

A 17.5-mg portion of the compound of Experimental Example 4 was dissolved in 10% pyridine-water and reacted with 20 µl of acetic anhydride for about 60 minutes and the product was purified in the same manner as in Experimental Example 4 to give 10.7 mg of a powder.

Mass analysis (M+H)$^+$: 1815.8600 (calculated value 1815.9743);
HPLC elution time: 19.7 minutes;
Column Conditions:
  Column: Wakosil 5C18 (4.6×100 mm)
  Eluent: Solution A (0.1% TFA-water)
    Solution B (0.1% TFA-containing 50% acetonitrile-water)
    Linear concentration gradient elution from solution A to solution B (25 minutes)
  Flow rate: 1.0 ml/minute.

EXPERIMENTAL EXAMPLE 7

Production of [Cys$^{17}$]-Human 19P2 Ligand (17–31)

The resin of Experimental Example 4 was further condensed with Boc-Cys(MeBzl) and the product was treated with hydrogen fluoride and the peptide purified by column chromatography in the same manner as in Experimental Example 4 to give 50 mg of a white powder.

Mass analysis (M+H)$^+$: 1737.9 (calculated value 1737.6);
HPLC elution time: 17.2 minutes;
Column Conditions:
  Column: Wakosil 5C18 (4.6×100 mm)
  Eluent: Solution A (0.1% TFA-water)
    Solution B (0.1% TFA-containing 50% acetonitrile-water)
    Linear concentration gradient elution from solution A to solution B (25 minutes)
  Flow rate: 1.0 ml/minute.

EXPERIMENTAL EXAMPLE 8

Production of [D-Ala$^{29}$]-Human 19P2 Ligand (1–31)

Following the same procedure as in Experimental Example 2, Boc-Phe and Boc-Arg(Tos) were introduced into the p-methylBHA resin in that order and then Boc-Gly was introduced in lieu of Boc-D-Ala. Thereafter, the same reaction procedure as in Experimental Example 2 was followed to give. Ser(Bzl)-Arg(Tos)-Thr(Bzl)-His(Bom)-Arg(Tos)-His(Bom)-Ser(Bzl)-Met-Glu(OcHex)-Ile-Arg(Tos)-Thr(Bzl)-Pro-Asp(OcHex)-Ile-Asn-Pro-Ala-Trp(CHO)-Tyr(Br-Z)-Ala-Ser(Bzl)-Arg(Tos)-Gly-Ile-Arg(Tos)-Pro-Val-D-Ala-Arg(Tos)-Phe-pMBHA resin. This resin was treated and the peptide purified in the same manner as in Experimental Example 2 to give Ser-Arg-Thr-His-Arg-His-Ser-Met-Glu-Ile-Arg-Thr-Pro-Asp-Ile-Asn-Pro-Ala-Trp-Tyr-Ala-Ser-Arg-Gly-Ile-Arg-Pro-Val-D-Ala-Arg-Phe-NH$_2$ as white powder.

Mass analysis (M+H)$^+$: 3678.6 (calculated value 3679.2);
HPLC elution time: 18.5 minutes;
Column Conditions:
  Column: YMC-A-301-3 ODS (4.6×100 mm)
  Eluent: Solution A (0.1% TFA-water)
    Solution B (0.1% TFA-containing 50% acetonitrile-water)
    Linear concentration gradient elution from solution A to solution B (25 minutes)
  Flow rate: 1.0 ml/minute.

EXPERIMENTAL EXAMPLE 9

Production of Bovine 19P2 Ligand (1–31)-Gly-Arg-OH

A commercial Boc-Arg(Tos)-OCH$_2$PAM resin (product of Applied Biosystems, currently Perkin Elmer) (0.83 g, 0.5 mmole) was placed in the reactor of a peptide synthesizer (Applied Biosystems model 430A), swollen with dichloromethane (DCM) and treated with 50% TFA/DCM to thereby eliminate the Boc group and liberate the amino group, followed by neutralization with DIEA. This amino group was condensed with the next amino acid Boc-Gly by the HOBt/DCC method. Thereafter, the same Boc-amino acids as used in Experimental Example 1 were subjected to serial condensation to give 1.21 g of a resin with the whole amino acid sequence introduced therein. A 0.59-gram portion of this resin was treated and the peptide purified in the same manner as in Experimental Example 1 to give 162 mg of a white powder.

Mass analysis (M+H)$^+$: 3789.0105 (calculated value 3788.9477);
HPLC elution time: 16.4 minutes;
Column Conditions:
  Column: Wakosil 5C18 (4.6×100 mm)
  Eluent: Solution A (0.1% TFA-water)
    Solution B (0.1% TFA-containing 50% acetonitrile-water)
    Linear concentration gradient elution from solution A to solution B (25 minutes)
  Flow rate: 1.0 ml/minute.

EXPERIMENTAL EXAMPLE 10

Production of Bovine 19P2 Ligand (1–31)-OH

Using a commercial Boc-Phe-OCH2PAM resin (product of Applied Biosystems, currently Perkin Elmer) (0.69 g, 0.5 mmole), Boc-amino acids were introduced therein successively according to the desired amino acid sequence. The product resin was purified and the peptide purified in the same manner as in Experimental Example 9 to give a white powder.

Mass analysis (M+H)$^+$: 3575.7451 (calculated value 3575.8254);
HPLC elution time: 16.6 minutes;
Column Conditions:
  Column: Wakosil 5C18 (4.6×100 mm)
  Eluent: Solution A (0.1% TFA-water)
    Solution B (0.1% TFA-containing 50% acetonitrile-water)
    Linear concentration gradient elution from solution A to solution B (25 minutes)
  Flow rate: 1.0 ml/minute.

EXPERIMENTAL EXAMPLE 11

Production of Bovine 19P2 Ligand (1–30)

Following the same procedure as in Experimental Example 2, the p-methylBHA resin was condensed with Boc-Arg(Tos), Boc-Gly, Boc-Val, Boc-Pro, Boc-Arg(Tos), Boc-Ile, Boc-Gly, Boc-Arg(Tos), Boc-Ser(Bzl), Boc-Ala, Boc-Tyr(Br-Z), Boc-Trp(CHO), Boc-Ala, Boc-Pro, Boc-Asn, Boc-Ile, Boc-Asp(OcHex), Boc-Pro, Boc-Thr(Bzl), Boc-Arg(Tos), Boc-Ile, Boc-Glu(OcHex), Boc-Met, Boc-Ser-(Bzl), Boc-His(Bom), Boc-Arg(Tos), Boc-His(Bom), Boc-Thr(Bzl), Boc-Arg(Tos) and Boc-Ser(Bzl) in that order, followed by treatment and purification in the same manner, to give a white powder.

Mass analysis (M+H)$^+$: 3517.4 (calculated value 3518.0);
HPLC elution time: 17.5 minutes;
Column Conditions:
Column: YMC-A-301-3 ODS (4.6×100 mm)
Eluent: Solution A (0.1% TFA-water)
Solution B (0.1% TFA-containing 50% acetonitrile-water)
Linear concentration gradient elution from solution A to solution B (25 minutes)
Flow rate: 1.0 ml/minute.

EXPERIMENTAL EXAMPLE 12

Production of [Cys$^{25}$]-Human 19P2 Ligand (12–25)

Following the same procedure as in Experimental Example 2, the p-methylBHA resin was condensed with Boc-Cys(MeBzl), Boc-Gly, Boc-Arg(Tos), Boc-Ser(Bzl), Boc-Ala, Boc-Tyr(Br-Z), Boc-Trp(CHO), Boc-Ala, Boc-Pro, Boc-Asn, Boc-Ile, Boc-Asp(OcHex), Boc-Pro and Boc-Thr(Bzl) in that order, followed by treatment and purification in the same manner, to give a white powder.

Mass analysis (M+H)$^+$: 1549.5 (calculated value 1549.7);
HPLC elution time: 15.3 minutes;
Column Conditions:
Column: Wakosil 5C18 (4.6×100 mm)
Eluent: Solution A (0.1% TFA-water)
Solution B (0.1% TFA-containing 50% acetonitrile-water)
Linear concentration gradient elution from solution A to solution B (25 minutes)
Flow rate: 1.0 ml/minute.

EXPERIMENTAL EXAMPLE 13

Production of Bovine 19P2 Ligand (12–31)

The resin obtained after condensation of Boc-Tyr(Br-Z) in Experimental Example 1 was further condensed with Boc-Trp(CHO), Boc-Ala, Boc-Pro, Boc-Asn, Boc-Ile, Boc-Asp (OcHEX), Boc-Pro and Boc-Thr(Bzl) in the same manner to give 1.14 g of Boc-Thr(Bzl)-Pro-Asp(OcHex)-Ile-Asn-Pro-Ala-Trp(CHO)-Tyr(Br-Z)-Ala-Gly-Arg(Tos)-Gly-Ile-Arg(Tos)-Pro-Val-Gly-Arg(Tos)-Phe-pMBHA resin. This resin was subjected to the hydrogen fluoride treatment and purification by column chromatography in the same manner as in Experimental Example 1–2) to give 60 mg of white powder.

Mass analysis (M+H)$^+$: 2242.149 (calculated value 2242.200);
HPLC elution time: 10.4 minutes;
Column Conditions:
Column: Wakosil 5C18 (4.6×100 mm)
Eluent: Solution A (0.1% TFA-containing 15% acetonitrile-water)
Solution B (0.1% TFA-containing 45% acetonitrile-water)
Linear concentration gradient elution from solution A to solution B (25 minutes)
Flow rate: 1.0 ml/minute.

EXAMPLE 2

Immunogen Preparation
(1) Preparation of 19P2 Ligand (18–31)-Containing Immunogen A complex was prepared from the [Cys$^{17}$]-19P2 ligand (17–31) obtained above in Example 1 (Experimental Example 7) and bovine thyroglobulin (BTG) and used as the immunogen. Thus, 20 mg of BTG was dissolved in 1.4 ml of 0.1 M phosphate buffer (pH 6.5) and the solution was mixed with 100 μl of a DMF solution containing 2.2 mg (8 μmol) of N-(γ-maleimidobutyryloxy)succinimide (GMBS) and the reaction was allowed to proceed at room temperature for 40 minutes. Thereafter, the mixture was fractionated using a Sephadex G-25 column, and 15 mg of the maleimido-containing BTG was mixed with 1.6 mg of [Cys$^{17}$]-19P2 ligand (17–31) and the reaction was allowed to proceed at 4° C. for 2 days. The reaction mixture was dialyzed against physiological saline at 4° C. for 2 days.

(2) Preparation of 19P2 Ligand (12–25)-Containing Immunogen

A complex was prepared from the [Cys$^{25}$]-19P2 ligand (12–25) obtained above in Example 1 (Experimental Example 12) and BTG and used as the immunogen. Thus, 21 mg of BTG was dissolved in 1.4 ml of 0.1 M phosphate buffer (pH 6.5), and the solution was mixed with 100 μl of a DMF solution containing 2.35 mg (8.4 μmol) of GMBS and the reaction was allowed to proceed at room temperature for 40 minutes. Thereafter, the mixture was fractionated using a Sephadex G-25 column, and 15 mg of the maleimido-containing BTG was mixed with 3.8 mg of [Cys$^{25}$]-19P2 ligand (12–25) and the reaction was allowed to proceed at 4° C. overnight. The reaction mixture was dialyzed against physiological saline at 4° C. for 3 days.

EXAMPLE 3

Immunization

Six to eight-week-old female BALB/C mice were subcutaneously immunized with the immunogens described above in Example 2, namely [Cys$^{17}$]-19P2 ligand (17–31)-BTG complex and [Cys$^{25}$]-19P2 ligand (12–25)-BTG complex, respectively, at a dose of about 20 μg/mouse, together with Freund's complete adjuvant. Thereafter, two or three booster immunizations were carried out with the same dose of the immunogen, together with Freund's incomplete adjuvant, at 3-week intervals.

EXAMPLE 4

Preparation of Enzyme-Labeled Antigens
(1) Preparation of Horseradish Peroxidase (HRP)-Labeled 19P2 Ligand (17–31)

[Cys$^{17}$]-19P2 ligand (17–31) obtained above in Example 1 (Experimental Example 7) was crosslinked to HRP (for enzyme immunoassay, product of Boehringer Mannheim) and the product was used as the labeled antigen for enzyme immunoassay (EIA). Thus, 6 mg (150 nmol) of HRP was dissolved in 0.95 ml of 0.1 M phosphate buffer, pH 6.5, the solution was mixed with 50 μL of a DMF solution containing 0.42 mg (1.5 μmol) of GMBS and the reaction was allowed to proceed at room temperature for 30 minutes, followed by fractionation on a Sephadex G-25 column. The thus-prepared maleimido-containing HRP (4.2 mg, 105 nmol) was mixed with 0.55 mg (315 nmol) of [Cys$^{17}$]-19P2 ligand (17–31) prepared in Example 1 (Experimental Example 7) and the reaction was allowed to proceed at 4° C. for 1 day, followed by fractionation on an Ultrogel AcA 44

(product of LKB-Pharmacia) column, to give HRP-labeled 19P2 ligand (17–31).

(2) Preparation of HRP-Labeled 19P2 Ligand (12–25)

[Cys$^{25}$]-19P2 ligand (12–25) obtained above in Example 1 (Experimental Example 12) was crosslinked to HRP and the product was used as the labeled antigen for EIA. Thus, 6 mg (150 nmol) of HRP was dissolved in 1.4 ml of 0.1 M phosphate buffer, pH 6.5, the solution was mixed with 100 µl of a DMF solution containing 0.42 mg (1.5 µmol) of GMBS and the reaction was allowed to proceed at room temperature for 30 minutes, followed by fractionation on a Sephadex G-25 column. The thus-prepared maleimido-containing HRP (4.2 mg, 105 nmol) was mixed with 0.48 mg (315 nmol) of [Cys$^{25}$]-19P2 ligand (12–25) prepared in Example 1 (12) and the reaction was allowed to proceed at 4° C. for 1 day, followed by fractionation on an Ultrogel AcA 44 column, to give HRP-labeled 19P2 ligand (12–25).

EXAMPLE 5

Antibody Titer Measurement (1) Measurement of Antibody Titer in Antiserum Derived from Mouse Immunized with [Cys$^{17}$]-19P2 Ligand (17–31)-BTG The antibody titers in mouse antisera during immunization with [Cys$^{17}$]-19P2 ligand (17–31)-BTG were measured by the same method. For preparing an anti-mouse immunoglobulin antibody-bound microplate, a 0.1 M carbonate buffer (pH 9.6) solution containing 100 µg/ml of an anti-mouse immunoglobulin antibody (IgG fraction, product of Cappel) was distributed in 100-µl portions into wells of a 96-well microplate and the plate was allowed to stand at 4° C. for 24 hours. The plate was then washed with phosphate-buffered saline (PBS, pH 7.4) and, for blocking excess binding sites on the wells, PBS containing 25% of BlockAce (product of Snow Brand Milk Products) was distributed in 300-µl portions into the wells, followed by at least 24 hours of treatment at 4° C.

To each well of the above anti-mouse immunoglobulin antibody-bound microplate were added 50 µl of buffer C [0.02 M phosphate buffer, pH 7.0, containing 1% BSA, 0.4 M NaCl and 2 mM EDTA] and 100 µl of a dilution, in buffer C, of mouse anti-[Cys$^{17}$]-19P2 ligand (17–31)-BTG antiserum, and the reaction was allowed to proceed at 4° C. for 16 hours. Then, said plate was washed with PBS, 100 µl of the HRP-labeled 19P2 ligand (17–31) prepared above in Example 4 (1) (300-fold diluted with buffer C) was added to each well, and the reaction was allowed to proceed at room temperature for 1 day. The plate was then washed with PBS, and the enzyme activity on each solid phase was determined by adding 100 µl of a TMB microwell peroxidase substrate system (product of Kirkegaard & Perry Lab., Inc., distributed by Funakoshi Yakuhin) and allowing the reaction to proceed at room temperature for 10 minutes. The reaction was terminated by adding 100 µl of 1 M phosphoric acid, and the absorption at 450 nm was measured on a plate reader (Bichromatic, product of Dainippon Pharmaceutical). The results thus obtained are shown in FIG. 1. In all eight mice immunized, an increase was observed in anti-19P2 ligand (17–31) antibody titer.

Figure 2:
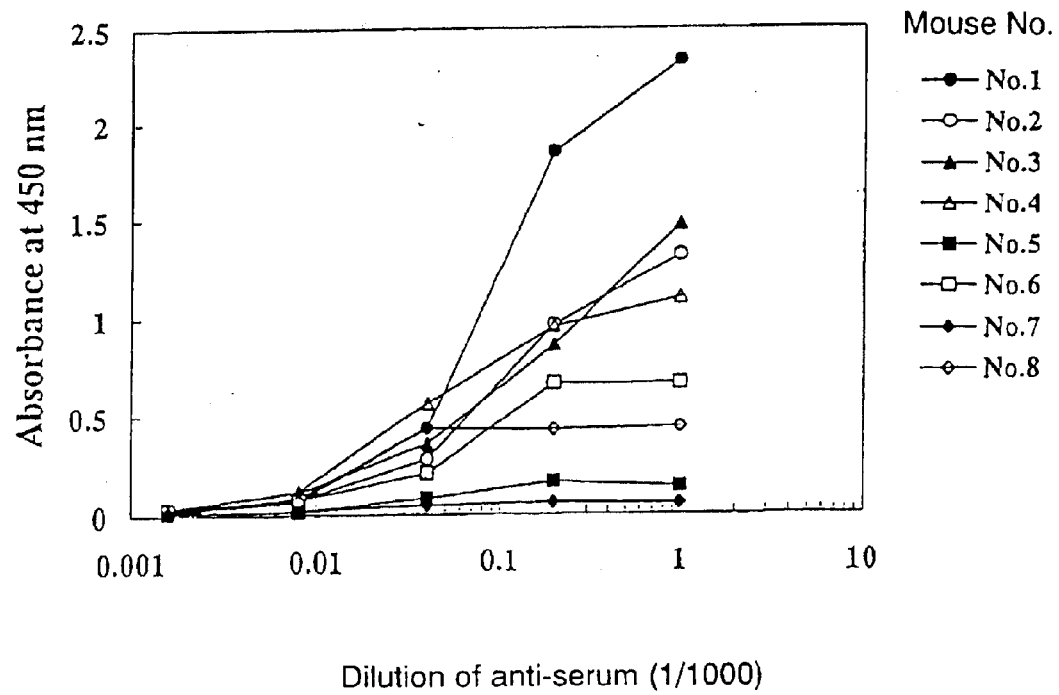

(2) Measurement of Antibody Titer in Antiserum Derived from Mouse Immunized with [Cys$^{25}$]-19P2 Ligand (12–25)-BTG The antibody titers in mouse antisera during immunization with [Cys$^{25}$]-19P2 ligand (12–25)-BTG were measured by the same method. To each well was added 100 µl of a dilution, in buffer C, of mouse anti-[Cys$^{25}$]-19P2 ligand (12–25)-BTG antiserum, and the reaction was allowed to proceed at 4° C. for 16 hours. Then, the plate was washed with PBS, 100 µl of the HRP-labeled 19P2 ligand (12–25) prepared above in Example 4 (2) (500-fold diluted with buffer C) was added, and the reaction was allowed to proceed at room temperature for 1 day. The plate was then washed with PBS, and the enzyme activity on each solid phase was determined by adding 100 µl of a TMB microwell peroxidase substrate system (Kirkegaard & Perry Lab., Inc., distributed by Funakoshi Yakuhin) and allowing the reaction to proceed at room temperature for 10 minutes. The reaction was terminated by adding 100 µl of 1 M phosphoric acid, and the absorption at 450 nm was measured on a plate reader (Bichromatic, product of Dainippon Pharmaceutical). The results thus obtained are shown in FIG. 2. In all eight mice immunized, an increase was observed in anti-19P2 ligand (12–25) antibody titer. The results are shown in FIG. 2. In three of the eight mice immunized, a relatively high antibody titer was observed.

EXAMPLE 6

Preparation of Monoclonal Anti-19P2 Ligand Antibodies

Mice that had shown relatively high antibody titer values were finally immunized by intravenously inoculating with a solution of 200 to 300 µg of the immunogen in 0.25 to 0.3 ml of physiological saline. Three to four days after the final immunization, the spleen was excised from each mouse, pressed with a stainless steel mesh and filtered, and splenocytes were suspended in Eagle's minimum essential medium (MEM), to give a splenocyte suspension. As the counterpart cells for cell fusion, BALB/C mouse-derived myeloma cells P3-X63.Ag8.U1 (P3U1) were used [Current Topics in Microbiology and Immunology, 81, 1 (1987)]. The cell fusion was carried out as originally described [Nature, 256, 495 (1975). Thus, the splenocytes and P3U1 were respectively washed with three portions of serum-free MEM, the splenocytes and P3U1 were mixed together in a ratio, in number, of 10:1, and the mixture was centrifuged at 800 revolutions per minute for 15 minutes to cause the cells to settle. The supernatant was removed to a sufficient extent, the sediment was loosened moderately, 0.3 ml of 45% polyethylene glycol (PEG) 6000 (product of Koch-Light) was added, and the mixture was allowed to stand in a warm water tank at 37° C. for 7 minutes to effect cell fusion. After fusion, a total of 15 ml of MEM was added to the cells at a rate of 2 ml per minute, then the mixture was centrifuged at 600 revolutions for 15 minutes and the supernatant was removed. This cell sediment was suspended in GIT medium (Wako Pure Chemical Industries) containing 10% fetal calf serum (GIT-10% FCS) to a P3U1 concentration of 2×10$^5$ cells per milliliter and the suspension was distributed in 1-ml portions into 192 wells on 24-well multidishes (product of Linbro). After this sowing, the cells were cultured in a 5% carbon dioxide gas incubator at 37° C. After 24 hours, HAT selection culture was started by adding 1 ml of GIT-10% FCS medium supplemented with HAT (hypoxanthine 1×10$^{-4}$ M, aminopterine 4×10$^{-7}$ M, thymidine 1.6×10$^{-3}$ M) (HAT medium) to each well. The HAT selection culture was continued while, on days 3, 6 and 9 after start of cultivation, 1 ml of each old medium was discarded and 1 ml of HAT medium was added. Hybridoma proliferation was observed after 9 to 14 days following cell fusion and, when the culture fluid turned yellow (about 1×10$^6$ cells/ml), each supernatant was collected and assayed for antibody titer by the method described in Example 5.

Figure 3:
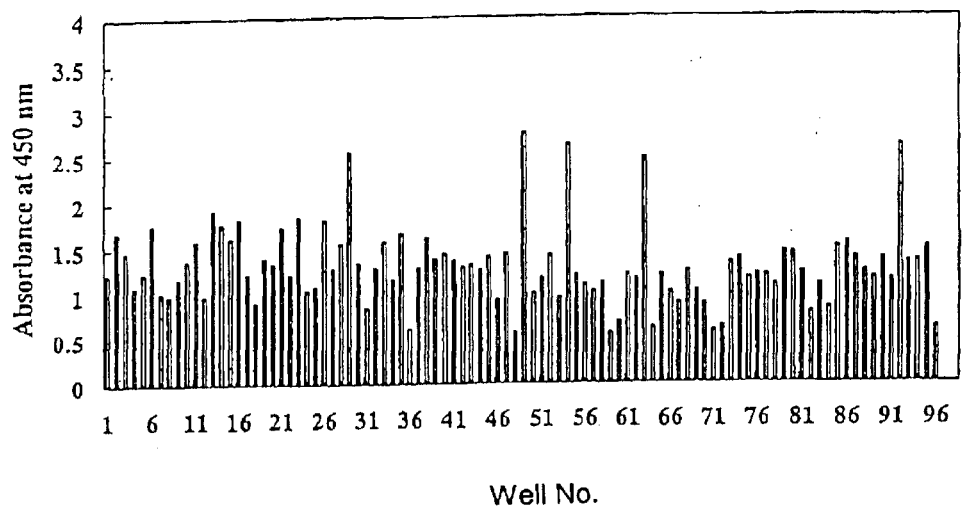
Figure 3:
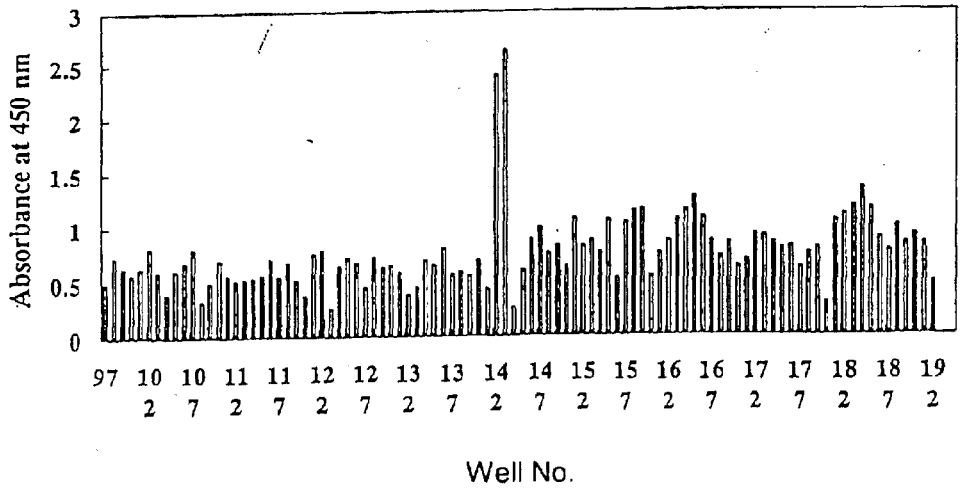

As a typical example of screening for hybridomas derived from mice immunized with [Cys$^{17}$]-19P2 ligand (17–31)-BTG, the results obtained using mouse No. 6 (cf. FIG. 1) are shown in FIG. 3. Including these, a total of two hybridoma strains were selected (Table 1).

TABLE 1

Reactivity features of anti-human 19P2 ligand (18–31) monoclonal antibodies
Reactivity 1)

| Hybridoma strain No. | h(1-31)n | h(1-31)-OH | b(1-31)n | Class/subclass | Note |
|---|---|---|---|---|---|
| 1 | + | − | + | IgG1, κ | P2L-1C |
| 2 | + | + | ± | | |
| 3 | + | − | + | | |
| 4 | + | + | ± | IgG1, κ | P2L-2C |
| 5 | ± | − | ± | | |
| 6 | + | + | ± | IgG1, κ | |
| 7 | + | − | + | IgG1, κ | |
| 8 | + | − | + | IgGM, κ | |

1) h(1-31)n stands for human 19P2-L31, h(1-31)-OH for human 19P2 ligand (1-31)-OH and b(1-31)n for bovine 19P2-L31.
2) When 100 nM antigen [human 19P2-L31, human 19P2 ligand (1-31)-OH or bovine 19P2-L31] was present,
+: $(B/B_0) < 0.50$;
±: $0.50 \leq (B/B_0) < 0.80$;
−: $0.80 \leq (B/B_0)$
where
B: Amount of HRP-labeled human 19P2 ligand (18–31) bound to the antibody in the presence of the antigen;
$B_0$: Amount of HRP-labeled human 19P2 ligand (18–31) bound to the antibody in the absence of the antigen.

Figure 4:
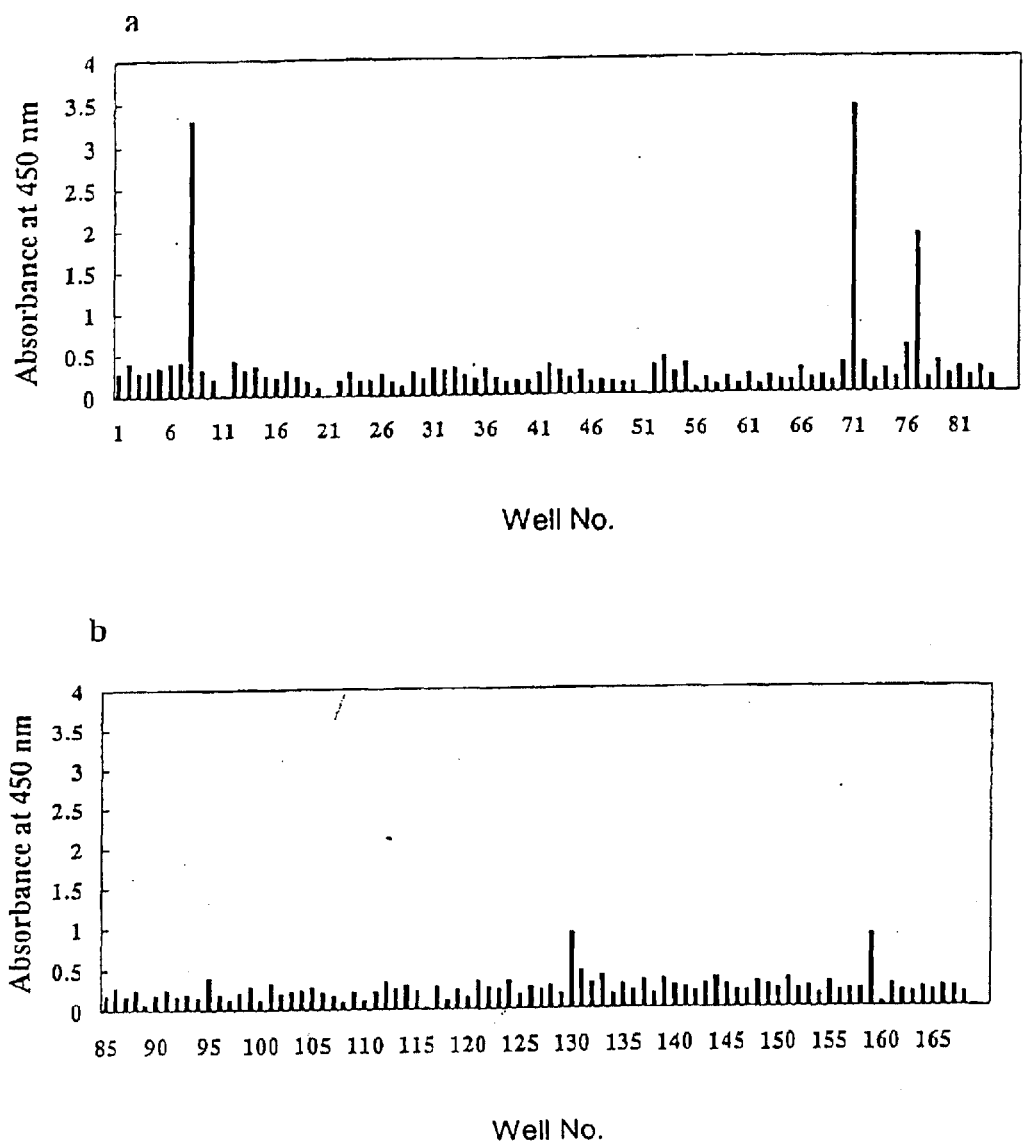

As a typical example of screening for hybridomas derived from mice immunized with [Cys$^{25}$]-19P2 ligand (12–25)-BTG, the results obtained using mouse No. 1 (cf. FIG. 2) are shown in FIG. 4. Including these, a total of three hybridoma strains were selected (Table 2).

TABLE 2

Reactivity features of anti-human 19P2 ligand (12–24) monoclonal antibodies
Reactivity 1)

| Hybridoma strain No. | h(1-31)n | h(12-31)n | r(1-31)n | Class/subclass | Note |
|---|---|---|---|---|---|
| 1 | + | + | + | IgG2b, κ | P2L-1T |
| 2 | + | + | + | IgG1, κ | P2L-3T |
| 3 | + | + | ± | IgG1, κ | P2L-2T |
| 4 | ± | ± | ± | | |
| 5 | + | + | ± | | |
| 6 | + | + | + | IgGM, κ | P2L-4T |
| 7 | − | − | ± | | |
| 8 | ± | ± | ± | | |
| 9 | − | − | ± | | |
| 10 | ± | + | ± | | |
| 11 | + | + | ± | | |
| 12 | − | − | ± | | |

1) h(1-31)n stands for human 19P2-L31, h(12-31)n for human 19P2-L20 and r(1-31)n for rat 19P2-L31.
2) When 10 nM antigen [human 19P2-L31, human 19P2-L20 or rat 19P2-L31] was present,
+: $(B/B_0) < 0.50$;
±: $0.50 \leq (B/B_0) < 0.75$;
−: $0.75 \leq (B/B_0)$
where
B: Amount of HRP-labeled human 19P2 ligand (12–24) bound to the antibody in the presence of the antigen;
$B_0$: Amount of HRP-labeled human 19P2 ligand (12–24) bound to the antibody in the absence of the antigen.

These hybridomas were then subjected to cloning by the limiting dilution method. In the cloning, BALB/C mouse thymocytes were added as feeder cells to a concentration of $5 \times 10^5$ cells per well. After cloning, hybridoma cells were intraperitoneally administered, in a dose of 1 to $3 \times 10^6$ cells/animal, to mice (BALB/C) intraperitoneally dosed with 0.5 ml of mineral oil beforehand and, 6 to 20 days later, the antibody-containing ascites was harvested.

The monoclonal antibody was purified from the ascites using a protein A column. Thus, 6 to 20 ml of the ascitic fluid was diluted with an equal volume of binding buffer (1.5 M glycine, pH 9.0, containing 3.5 M NaCl and 0.05% NaN$_3$) and the dilution was applied to a recombinant protein A-agarose (product of Repligen) column equilibrated in advance with binding buffer and the specific antibody was eluted with elution buffer (0.1 M citrate buffer, pH 3.0, containing 0.05% NaN$_3$). The eluate was dialyzed against PBS at 4° C. for 2 days, then subjected to sterilizing filtration through a 0.22 μm filter (product of Millipore) and stored at 4° C. or −80° C. In determining the class/subclass of the monoclonal antibody, the technique of enzyme-linked immunosorbent assay (ELISA) using a purified monoclonal antibody-bound solid phase was employed. Thus, 0.1 M carbonate buffer, pH 9.6, containing 2 μg/ml of antibody was distributed in 100-μl portions into wells of a 96-well microplate and the plate was allowed to stand at 4° C. for 24 hours. The excess binding sites on each well were blocked with BlockAce by the method described above in Example 5 and then the class/subclass of the antibody immobilized on the solid phase was determined by ELISA using an isotype typing kit (Mouse-Typer TM Sub-Isotyping Kit, product of Bio-Rad).

EXAMPLE 7

Competitive Enzyme Immunoassay
(1) Competitive EIA (1)

Figure 5:
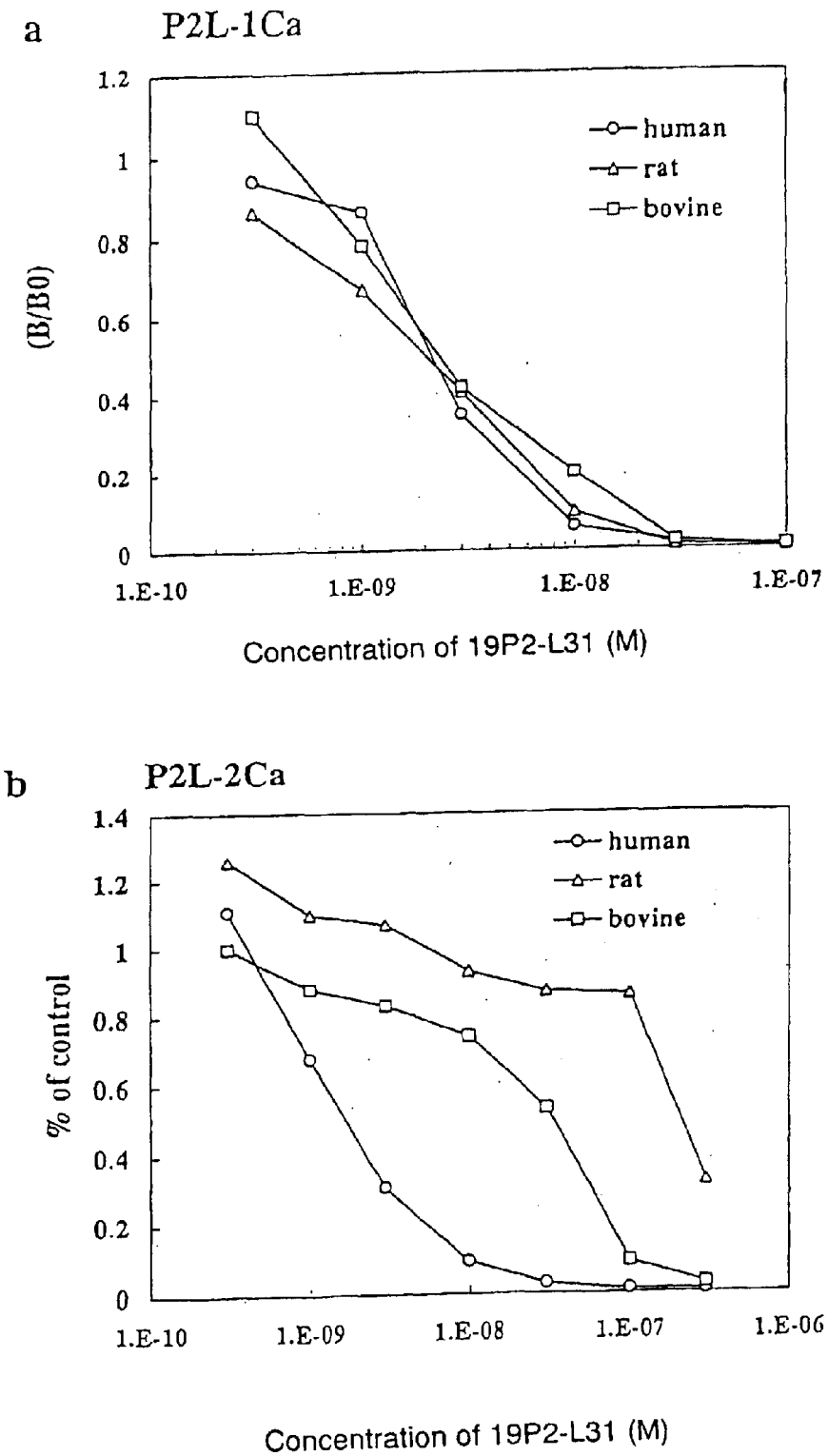
Figure 6:
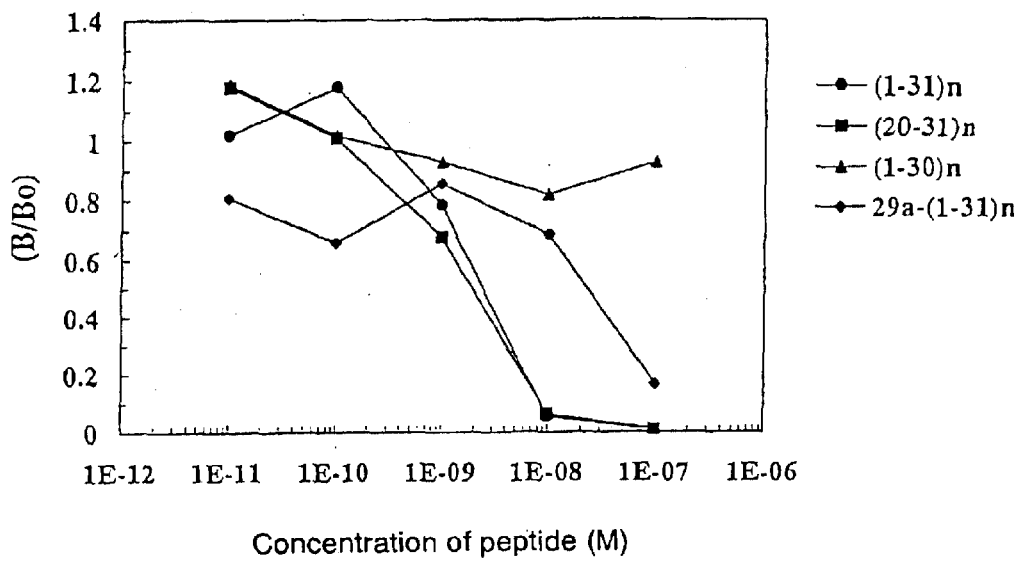
Figure 6:
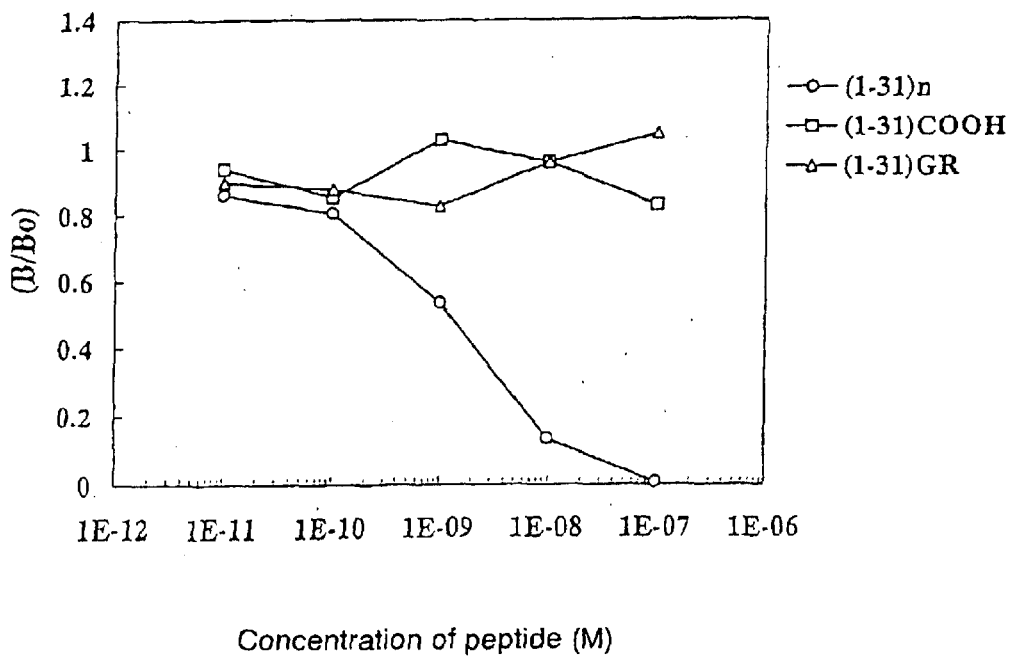

The monoclonal antibodies produced by using [Cys$^{17}$]-19P2 ligand (17–31)-BTG as the immunogen were examined for their reaction specificity by the following method. First, the antibody titers of various solutions of each monoclonal antibody were examined by the method described in Example 5 (1), and the antibody concentration (about 30 to 50 ng/ml) at which the amount of the label bound was about 50% of the level of saturation was selected as the antibody concentration for use in competitive EIA. Then, 50 μl of each antibody solution diluted with buffer C to a predetermined concentration, 50 μl of a solution, in buffer C, of human, rat or bovine 19P2 ligand (1–31) or a 19P2 ligand partial peptide, namely human 19P2 ligand (1–30), human [D-Ala$^{29}$]-19P2 ligand (1–31), human 19P2 ligand (20–31), bovine 19P2 ligand (1–31)-OH or bovine 19P2 ligand (1–31)-Gly-Arg-OH, and 50 μl of the HRP-labeled 19P2 ligand (17–31) mentioned above in Example 4 (1) (400-fold diluted with buffer C) were added to each well of the anti-mouse immunoglobulin antibody-bound microplate described above in Example 5, and the reaction was allowed to proceed at 4° C. for 16 hours. Thereafter, the plate was washed with PBS, and the enzyme activity on each solid phase was measured by the method described above in Example 5 (1). The results are shown in Table 1. All the antibodies reacted with the HRP-labeled 19P2 ligand (17–31) and had reactivity against human 19P2 ligand (1–31) as well (Table 1). Of four monoclonal antibodies initially selected, two reacted with bovine and rat 19P2 ligand (1–31) species as well to almost the same extent. As a typical example, the results of competitive EIA as obtained with the monoclonal antibody P2L-1Ca (IgG1, κ), which showed the highest reactivity against human, rat and bovine 19P2 ligand (1–31) species among the monoclonal antibodies examined, are shown in FIG. 5(*a*). It is seen that these antibodies have almost the same reactivity against human, rat and bovine 19P2 ligand (1–31) species. From the standard curve for P2L-1C and human 19P2 ligand (1–31), it was found that the 19P2 ligand (1–31) concentration giving (B/B0)=0.5 is 3 nM or 1.1 ng/well. Further, since this antibody P2L-1C shows reactivity, though weak, with human [D-Ala$^{29}$]-19P2 ligand (1–31) but does not show cross-reactivity against human 19P2 ligand (1–30), bovine 19P2 ligand (1–31)-OH or bovine 19P2 ligand (1–31)-Gly-Arg-OH, it was found that it recognizes a C-terminal partial structure of 19P2 ligand (1–31), namely the 31st residue Phe and the C-terminal amide [FIG. 6(a)]. On the other hand, the results of competitive EIA as obtained by using P2L-2C are shown in FIG. 5(b). It was found that the reactivity of P2L-2C (IgG1, κ) against human 19P2 ligand (1–31) (antigen concentration giving (B/B0)=0.5: 1.5 nM, 0.5 ng/well) is 33 times the reactivity against bovine 19P2 ligand (1–31) (antigen concentration giving (B/B0)=0.5: 50 nM, 18 ng/well) and 130 times the reactivity against rat 19P2 ligand (1–31) (antigen concentration giving (B/B0)= 0.5: 200 nM, 73 ng/well). From these results, it is presumable that P2L-2C strongly recognizes the 21st residue Ala and the 22nd residue Ser of 19P2 ligand (1–31) differing in sequence among human, bovine and rat.

(2) Competitive EIA (2)

Figure 7:
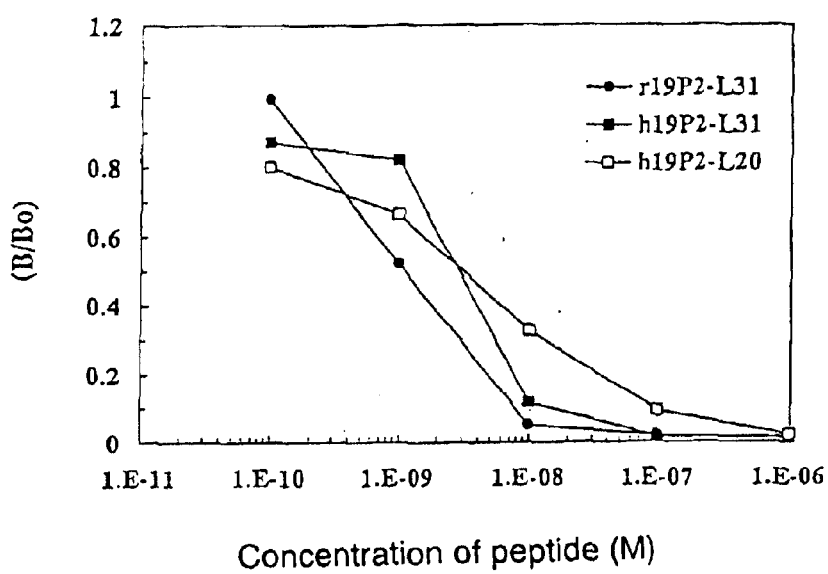
Figure 7:
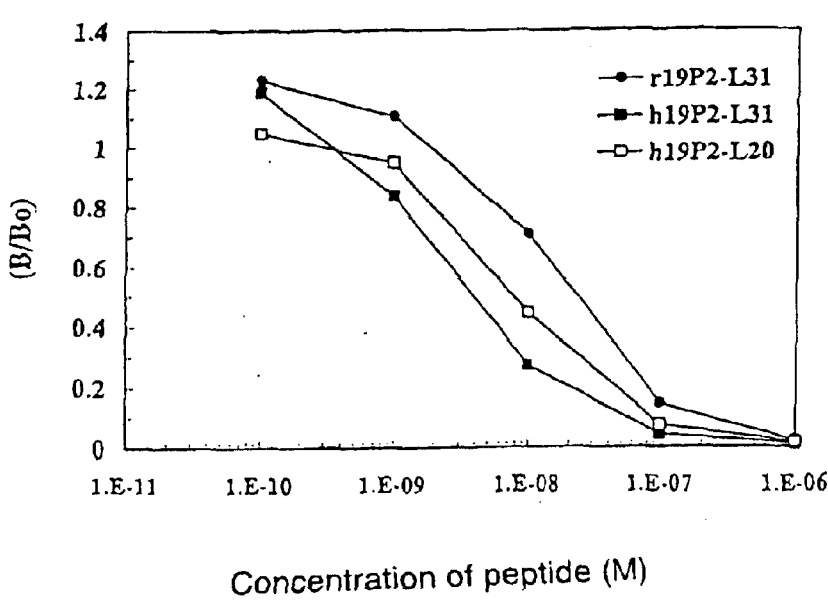
Figure 8:
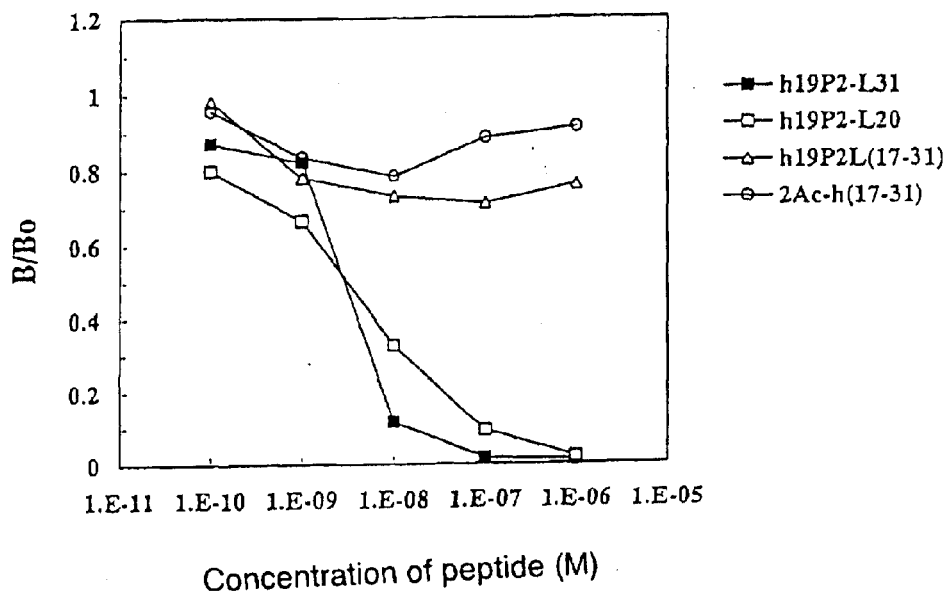
Figure 8:
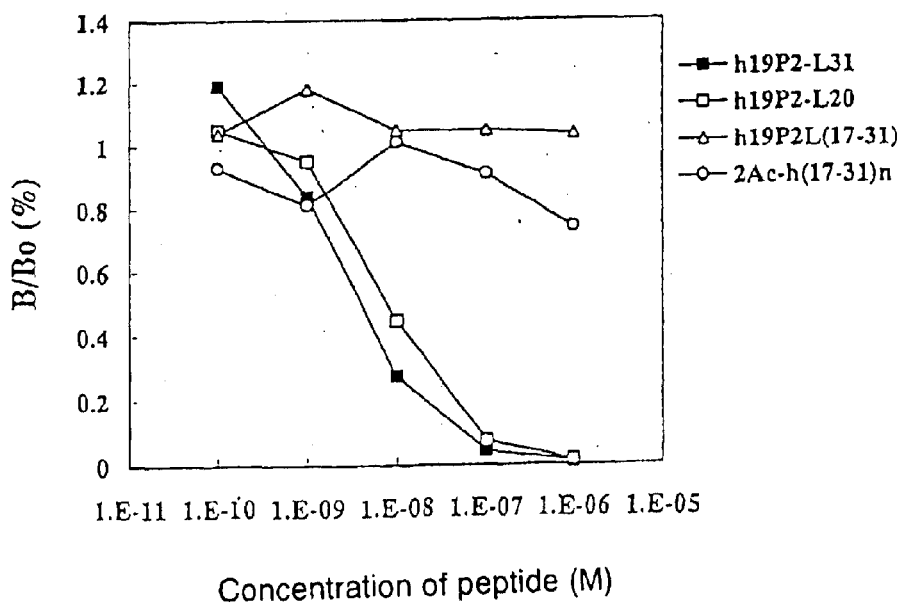
Figure 9:
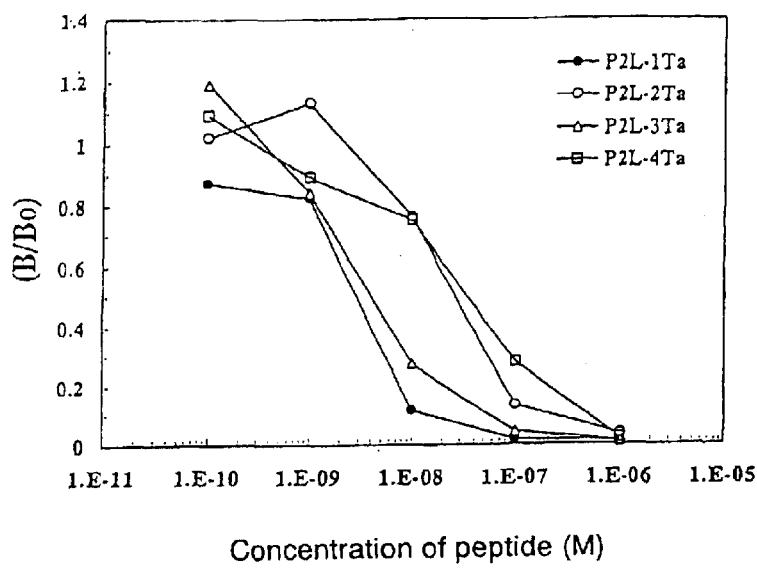

The reaction specificity of the anti-[Cys$^{25}$]-19P2 ligand (12–25)-BTG monoclonal antibody was studied by the same method. First, the antibody titers of various solutions of each monoclonal antibody were examined by the method described in Example 5 (2), and the antibody concentration (about 30 to 50 ng/ml) at which the amount of the label bound was about 50% of the level of saturation was selected as the antibody concentration for use in competitive EIA. Then, 50 µl of each antibody solution diluted with buffer C to a predetermined concentration, 50 µl of a solution, in buffer C, of human, rat or bovine 19P2 ligand (1–31) or a 19P2 ligand partial peptide, namely human 19P2 ligand (12–31), human 19P2 ligand (17–31) or diacetylated human 19P2 ligand (17–31), and 50 µl of the HRP-labeled 19P2 ligand (12–25) mentioned above in Example 4 (2) (500-fold diluted with buffer C) were added to each well of the anti-mouse immunoglobulin antibody-bound microplate, and the reaction was allowed to proceed at 4° C. for 16 hours. Thereafter, the plate was washed with PBS, and the enzyme activity on each solid phase was measured by the method described above in Example 5 (1). The results are shown in Table 2. All the antibodies reacted with the HRP-labeled 19P2 ligand (12–31) and had reactivity against human 19P2 ligand (1–31) and rat 19P2 ligand (1–31) as well. As typical examples, the results of competitive EIA as obtained with the monoclonal antibodies P2L-1Ta (IgG$_{2b}$, κ) and P2L-3Ta (IgG$_1$, κ), which were highest in reactivity against human and rat 19P2 ligand (1–31) species among the monoclonal antibodies examined, are shown in FIG. 7. From the standard curve for P2L-1Ta and human 19P2 ligand (1–31), it was found that the human 19P2 ligand (1–31) concentration giving (B/B0)=0.5 is 4 nM or 1.6 ng/well. Further, it was found that the reactivity of P2L-1Ta against 19P2 ligand (12–31) (antigen concentration giving (B/B0)= 0.5: 4 nM, 0.88 ng/well) is of the same order as against human 19P2 ligand (1–31) and the reactivity thereof against rat 19P2 ligand (1–31) (antigen concentration giving (B/B0)=0.5: 1 nM, 0.4 ng/well) is 4 times higher [FIG. 7(a)]. On the other hand, as for the reactivity of P2L-3Ta against 19P2 ligand, it was found that the human 19P2 ligand (1–31) concentration giving (B/B0)=0.5 is 4 nM, 1.6 ng/well. It was further found that the reactivity of P2L-1Ta against 19P2 ligand (12–31) (antigen concentration giving (B/B0)=0.5: 7 nM, 1.54 ng/well) is half the reactivity against human 19P2 ligand (1–31) and the reactivity against rat 19P2 ligand (1–31) (antigen concentration giving (B/B0)=0.5: 25 nM, 0.4 ng/well) is 6 times higher [FIG. 7(b)]. Since neither of the antibodies showed cross-reactivity against human 19P2 ligand (17–31) or 2Ac-human 19P2 ligand (17–31), it was found that they recognize the partial structure comprising 19P2 ligand (12–16) (FIG. 8). In FIG. 9, there are shown, in addition to the standard curves for these two antibodies, the standard curves for human 19P2 ligand (1–31) as constructed by using other two initially selected monoclonal antibodies showing high reactivity against human 19P2 ligand (1–31), namely P2L-2Ta and P2L-4Ta, in competitive EIA. The human 19P2 ligand (1–31) concentration giving (B/B0)=0.5 for these antibodies are within the range of 3 to 50 nM, and the competitive EIA using P2L-1Ta is most sensitive, namely about 0.1 nM [(B/B0)=0.9] human 19P2 ligand (1–31) could be detected.

EXAMPLE 8

Preparation of HRP-Labeled Anti-19P2 Ligand Monoclonal Antibody (1) P2L-1Ta-HRP

To a solution of 18 mg (120 nmol) of a purified P2L-1Ta fraction in 0.1 M phosphate buffer, pH 6.8, was added 50 µl of DMF containing 1.43 µmol of GMBS, and the reaction was allowed to proceed at room temperature for 40 minutes. The reaction mixture was treated for separation on a Sephadex G-25 column (eluent: 0.1 M phosphate buffer, pH 6.7) to give 13 mg of a maleimide-containing antibody fraction. Then, 60 µl of DMF containing 5.8 µmol of N-succinimidyl-3-(2-pyrimidyldithio)propionate (SPDP) was added to 1.4 ml of 0.02 M phosphate buffer (pH 6.8) containing 15.5 mg (387 nmol) of HRP (containing 0.15 M NaCl as well), and the reaction was allowed to proceed at room temperature for 40 minutes. Then, 0.4 ml of 0.1 M acetate buffer (pH 4.5) containing 68 µmol of dithiothreitol was added, the reaction was allowed to proceed at room temperature for 20 minutes and the mixture was treated for separation on a Sephadex G-25 column (eluent: 0.1 M phosphate buffer, pH 6.0, containing 2 mM EDTA), to give 11 mg of HRP having an SH group introduced therein. Then, 8 mg of the SH-containing HRP and 3 mg of the maleimido-containing antibody fraction were mixed together, the mixture was concentrated to about 0.5 ml using a collodion bag (product of Sartorius) and the concentrate was allowed to stand at 4° C. for 16 hours. The reaction mixture was applied to a Sephacryl S-300HR column (product of Pharmacia), and the P2L-1Ta-HRP conjugate fraction was purified by elution using 0.1 M phosphate buffer, pH 6.5, as the eluent.

(2) P2L-3Ta-HRP

Using 15 mg of a purified P2L-3Ta fraction and 16 mg of HRP, a P2L-3Ta-HRP conjugate was prepared in the same manner as described above.

EXAMPLE 9

Sandwich EIA (1) Specificity and Sensitivity of Sandwich EIA using P2L-1Ta-HRP

A solution, in 0.1 M carbonate buffer, pH 9.6, of 10 µg/ml of the monoclonal antibody P2L-1Ca purified as described above in Example 6 was distributed in 100-µl portions into wells of a 96-well microplate and allowed to stand at 4° C. for 24 hours. Excess binding sites on each well was inactivated by adding 400 µl of BlockAce 4 times diluted with PBS.

Figure 10:
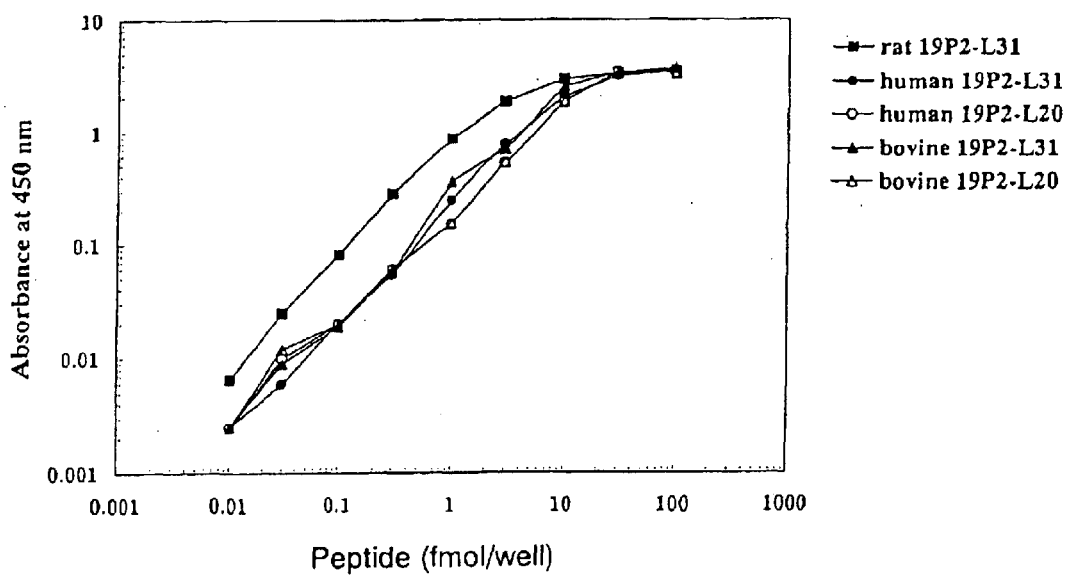
Figure 11:
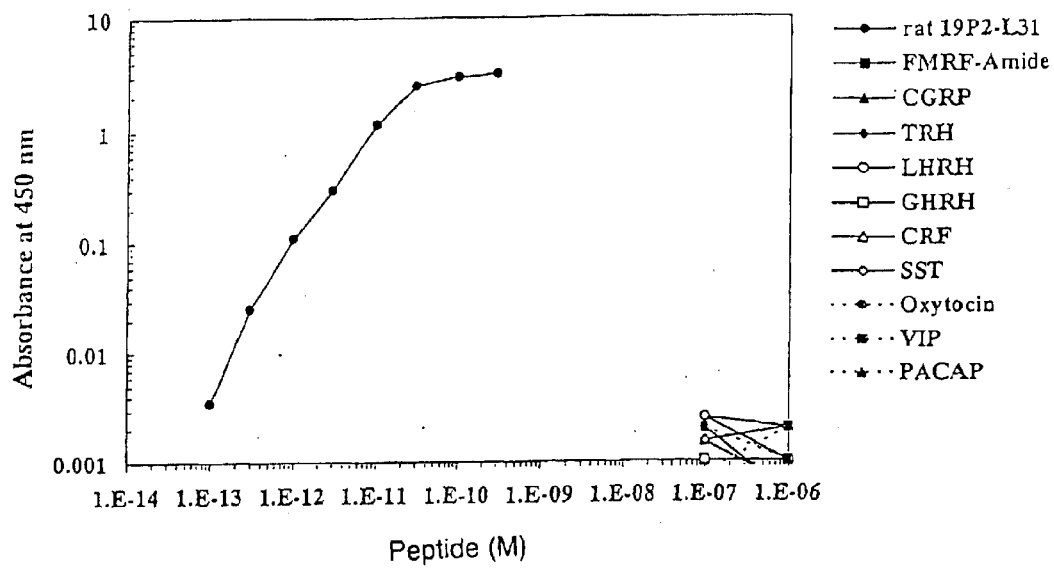

To each well of the plate prepared in the above manner was added 100 µl of a standard 19P2 ligand (1–31) solution diluted with buffer EC [0.02 M phosphate buffer, pH 7, containing 10% BlockAce, 0.2% BSA, 0.4 M NaCl and 0.05% CHAPS [3-(cholamidopropyl)dimethylammonio]-propanesulfonic acid], and the reaction was allowed to proceed at 4° C. for 24 hours. After washing with PBS, 100 µl of P2L-1Ta-HRP prepared as described above in Example 8 (20,000-fold diluted with buffer C) was added and reaction was allowed to proceed at 4° C. for 24 hours. A 30,000-fold dilution was used as the labeled antibody concentration. After washing with PBS, the enzyme activity on the solid phase was determined by the method described above in Example 5 using TMB (enzyme reaction period: 20 minutes). The results are shown in FIG. 10. It was found that 19P2 ligand (1–31) can be detected with very high sensitivity. Thus, this sandwich EIA can detect 0.1 fmol/well of human 19P2 ligand (1–31) or 19P2 ligand (12–31), 0.1 fmol/well of bovine 19P2 ligand (1–31) or 19P2 ligand (12–31), and 0.03 fmol/well of rat 19P2 ligand (1–31). The assay did not detect any of other hypothalamic peptides, namely TRH, LHRH, GHRH, CRF, SST and oxytocin (FIG. 11). Therefore, the sandwich EIA using P2L-1C as the solid phase antibody and P2L-1Ta-HRP as the labeled antibody can detect 19P2 ligand (1–31) and 19P2 ligand (12–31) with very high sensitivity and selectivity, irrespective of animal species.

(2) Specificity and Sensitivity of Sandwich EIA using P2L-3Ta-HRP

Figure 12:
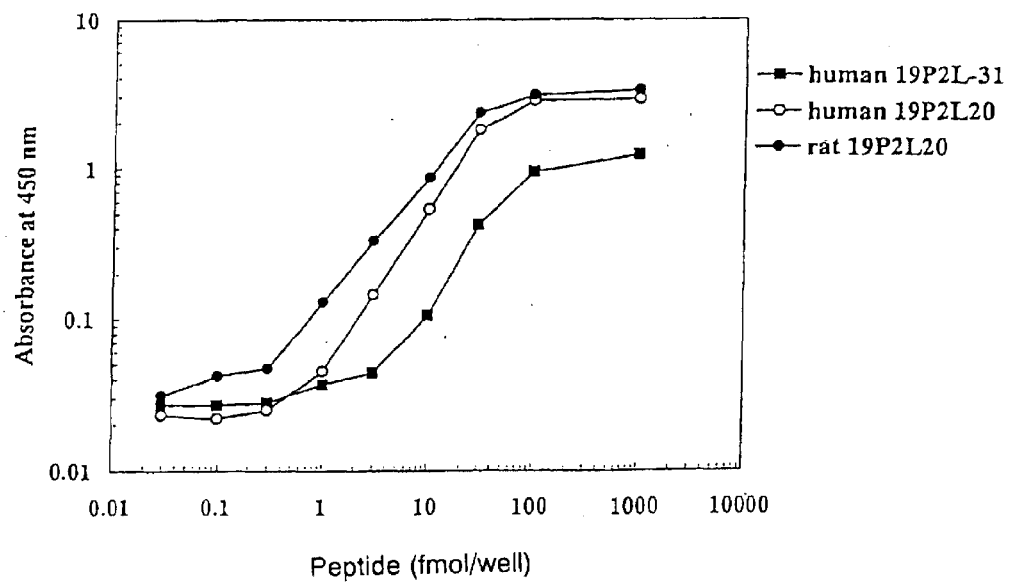

The specificity and sensitivity of the sandwich assay using P2L-1Ca as the solid phase antibody and the P2L-3Ta-HRP prepared as described above in Example 8 (2) as the labeled antibody were studied. The reactivities against human 19P2 ligand (1–31), 19P2 ligand (12–31) and rat 19P2 ligand (1–31) were examined in the same manner as in Example 9 (1) described above. A 1,000-fold dilution was used as the labeled antibody concentration (FIG. 12). As a result, the sandwich EIA using P2L-3Ta-HRP could detect 0.3 fmol/well of human 19P2 ligand (1–31), 1 fmol/well of 19P2 ligand (12–31) and 3 fmol/well of rat 19P2 ligand (1–31). However, it was 3 to 10 times lower in sensitivity as compared with the sandwich EIA using P2L-1Ta-HRP.

EXAMPLE 10

Neutralization of Biological Activity of 19P2 Ligand (1–31) by P2L-1Ca

Figure 13:
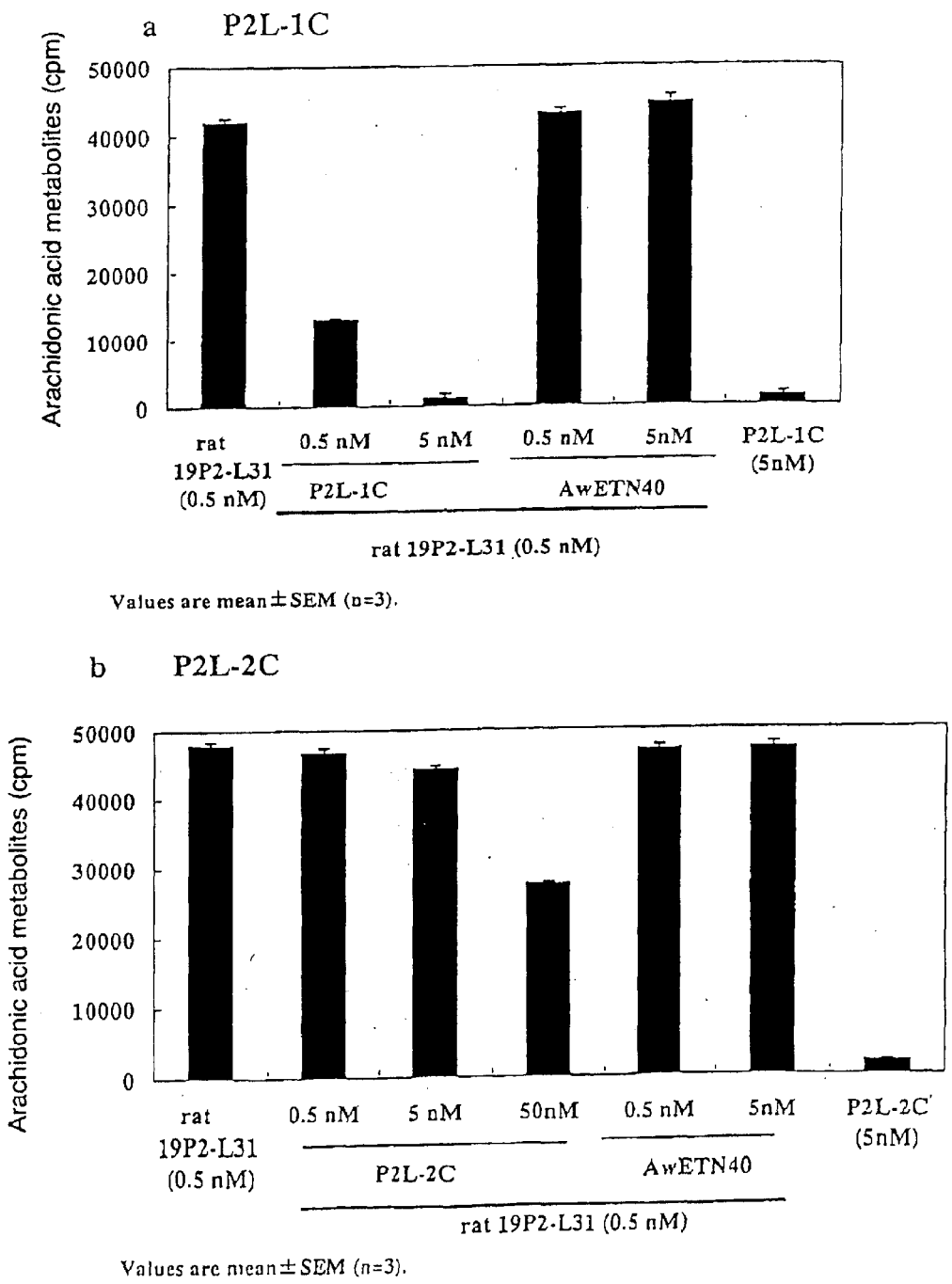

The neutralizing activity of P2L-1Ca against 19P2 ligand (1–31) was examined in an arachidonic acid metabolite releasing activity assaying system using 19P2 receptor expressing CHO cells. Thus, P2L-1Ca, P2L-3Ca, and anti-endothelin monoclonal antibody (AwETN40) (control antibody) having the same IgG subclass structure (IgG$_1$, κ) as P2L-1Ca were diluted to various concentrations. Each dilution was incubated with rat 19P2 ligand (1–31) (5×10$^{-10}$ M) at room temperature for 1 hour and then the residual activity was determined using 19P2 receptor expressing CHO cells. For arachidonic acid metabolite releasing activity assaying, 19P2 receptor expressing CHO cells were sowed on a 24-well plate in an amount of 0.5×10$^5$ cells/well and, after 24 hours of incubation, [$^3$H]arachidonic acid was added to a concentration of 0.5 µCi/well. At 24 hours after the addition of [$^3$H]arachidonic acid, cells were washed with MEM containing 0.1% BSA, and a mixed solution of one of the above monoclonal antibodies and rat 19P2 ligand (1–31) was added in an amount of 500 µl/well. After 1 hour of incubation at 37° C., a 400-µl portion of the 500 µl of reaction mixture was added to 4 ml of a scintillator, and the amount of [$^3$H]arachidonic acid metabolites released into the reaction mixture was monitored with a scintillation counter (FIG. 13). As a result, P2L-1Ca inhibited the activity of 19P2 ligand (1–31) by 75% at 5×10$^{-10}$ M and by 100% at 5×10$^{-9}$ M (FIG. 13a). On the other hand, P2L-2Ca suppressed the activity of 19P2 ligand (1–31) only by about 40% at 5×10$^{-8}$ M (FIG. 13b). In view of the foregoing, it was revealed that P2L-1Ca neutralizes the arachidonic acid metabolite releasing activity of 19P2 ligand (1–31).

EXAMPLE 11

Assay of 19P2 Ligand (1–31) in Plasma

Rat plasma (1 ml) was concentrated and pretreated using 265 mg of Sep-Pak Plus C18 cartridge (product of waters) and then assayed for 19P2 ligand (1–31) by the sandwich EIA described above in Example 9. In the plasma pretreatment, the Sep-Pak Plus C18 cartridge activated by passing therethrough 4 ml of 86% ethanol containing 4% acetic acid, 4 ml of methanol, 4 ml of distilled water and 4 ml of 4% acetic acid in that order was loaded with 1 ml of plasma acidified by addition of 3 ml of 4% acetic acid. After the addition, the cartridge was washed with 10 ml of distilled water and then eluted with 4 ml of 86% ethanol containing 4% acetic acid and 4 ml of methanol, and the elute was concentrated at 37° C. in a nitrogen gas atmosphere. The concentrated fraction was reconstituted with 0.25 ml of buffer C and assayed by sandwich EIA. The results are shown in Table 3. It was found that the rat plasma contained 0.2±0.03 fmol/ml (mean±SEM, n=8) of 19P2 ligand (1–31).

TABLE 3

| Assay of 19P2 ligand in rat plasma Reactivity 1) | |
|---|---|
| Rat No. | Immunoreactive 19P2 ligand (fmol/ml) |
| 1 | 0.25 |
| 2 | 0.11 |
| 3 | 0.21 |
| 4 | 0.21 |
| 5 | 0.10 |
| 6 | 0.05 |
| 7 | 0.04 |
| 8 | 0.19 |
| 9 | 0.21 |
| 10 | 0.13 |
| Mean ± SD | 0.15 ± 0.07 |

EXAMPLE 12

Detection of 19P2 Ligand in Rat Plasma by Reversed Phase High-Performance Liquid Chromatography (RP-HPLC)

For identifying the molecular species of 19P2 ligand contained in the rat plasma described above in Example 11, 50 ml of the rat plasma was partially purified by the method described above in Example 11 and this eluate fraction was concentrated and then fractionated by reversed phase HPLC using ODS-80 TM.

Column Conditions

Column: ODS-80 TM (4.6×250 mm)

Eluent: Solution A (0.05% trifluoroacetic acid-containing 5% acetonitrile)

Solution B (0.05# trifluoroacetic acid-containing 60% acetonitrile)

Elution mode: The proportion of eluent B was increased from 0% to 35% within the first 5 minutes and then linearly increased from 35% to 48% over 30 minutes.

Flow rate: 1.0 ml/min.

Fractionation: 0.5 ml/tube.

Figure 14:
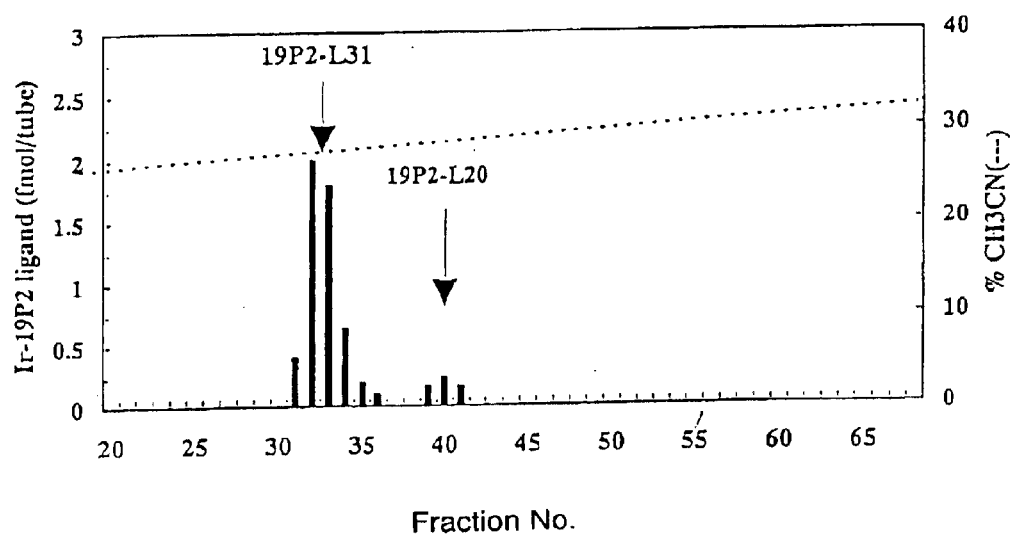

Each eluate fraction was subjected to centrifugal concentration to dryness under reduced pressure, the concentrate was dissolved in 250 ml of buffer C and the solution was subjected to the sandwich EIA described above in Example 10. The results are shown in FIG. 14. The immunological activity of 19P2 ligand in plasma was mostly eluted at the position of elution of synthetic 19P2 ligand (1–31), hence it was confirmed that said sandwich EIA detected 19P2 ligand (1–31). Therefore, it is expected that this assay system will provide an important tool for exploring the changes or fluctuation in plasma 19P2 ligand level.

INDUSTRIAL APPLICABILITY

The monoclonal antibodies (in particular P2L-1Ca) to the 19P2 ligand as provided by the invention have very high binding ability and can neutralize the arachidonic acid metabolite releasing activity of the 19P2 ligand. Therefore, they can be used, among others, as diagnostic, prophylactic and/or therapeutic agents for various diseases caused by some or other abnormality in the pituitary function modulating activity (e.g. prolactin secretion promoting activity), central nervous system modulating activity and pancreatic function modulating activity, among others, supposedly possessed by the 19P2 ligand.

The immunoassay method using the monoclonal antibodies of the invention by the sandwich technique (in particular the sandwich technique using one of the monoclonal antibodies mentioned above and an antibody recognizing an intermediate portion of the 19P2 ligand) can assay the 19P2 ligand or a derivative thereof specifically and with high sensitivity. This assay method can be used in elucidating the physiological functions of the 19P2 ligand or a derivative thereof.

What is claimed is:

1. A monoclonal antibody that specifically binds to a peptide having an amino acid sequence of residues 12 to 24 of SEQ ID NO: 2.

2. The monoclonal antibody as claimed in claim 1 which is a mouse IgG.

3. A method of detecting 19P2 ligand in a test fluid which comprises using the monoclonal antibody of claim 1 in an assay, said assay comprising:

contacting the test fluid sample with said monoclonal antibody, detecting any complexes form from the binding of said 19P2 ligand with said monoclonal antibody, and relating the present or amount of said complexes to the present or amount of 19P2 ligand in said sample.

4. An isolated hybridoma cell producing the monoclonal antibody of claim 1.

5. The monoclonal antibody of claim 1, which specifically binds with a peptide having the amino acid sequence of SEQ ID NO: 11.

6. A method for detecting 19P2 ligand in a sample, comprising:

contacting said sample with the monoclonal antibody of claim 5, and detecting any complexes form from the binding of said 19P2 ligand to said monoclonal antibody, and relating the present or amount of said complexes to the present or amount of 19P2 ligand in said sample.

7. The method of claim 6, further comprising: assaying said sample wherein said 19P2 ligand is attached to a carrier.

8. The method of claim 6 wherein said monoclonal antibody is attached to a carrier.

9. The method of claim 6 wherein said monoclonal antibody is attached to a detectable signal or label.

10. The method of claim 6 which is a sandwich assay.

11. The method of claim 6 which is a competitive inhibition assay.

12. The method of claim 6 in which the monoclonal antibody is P2L-1Ta.

13. A method for detecting 19P2 ligand in a sample, comprising:

contacting said sample with the monoclonal antibody of claim 5 and a second antibody comprising an antibody which specifically binds to a peptide having the amino acid sequence of SEQ ID NO: 7, and detecting any complexes form from the binding of the monoclonal antibody of claim 5, said 19P2 ligand and said second antibody, and relating the present or amount of said complexes to the present or amount of 19P2 ligand in said sample.

14. The monoclonal antibody of claim 1, which specifically binds with a peptide having the amino acid sequence of SEQ ID NO: 1, SEQ ID NO: 2, SEQ ID NO: 3, SEQ ID NO: 5, or SEQ ID NO: 12.

15. The monoclonal antibody of claim 1, which specifically binds with a peptide having the amino acid sequence of amino acid residues 12 to 24 or SEQ ID NO: 1, amino acid residues 12 to 24 of SEQ ID NO: 2, or amino acid residues 12 to 24 of SEQ ID NO: 3.

16. The monoclonal antibody of claim 1, which specifically binds with a 19P2 ligand peptide, but which does not bind with a peptide having the amino acid sequence of SEQ ID NO: 4 or SEQ ID NO: 6.

17. The monoclonal antibody of claim 1, which is P2L-1Ta, as secreted by hybridoma NIBII 6300.

18. An isolated hybridoma cell line, having accession number NIBH 6300, said cell line producing the antibody P2L-1Ta.

* * * * *

SEQUENCE LISTING

<160> NUMBER OF SEQ ID NOS: 13

<210> SEQ ID NO 1
<211> LENGTH: 31
<212> TYPE: PRT
<213> ORGANISM: Bovine
<220> FEATURE:
<221> NAME/KEY: PEPTIDE
<222> LOCATION: (31)..(31)
<223> OTHER INFORMATION: Phe-NH2

<400> SEQUENCE: 1

Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Xaa
            20                  25                  30

<210> SEQ ID NO 2
<211> LENGTH: 31
<212> TYPE: PRT
<213> ORGANISM: human
<220> FEATURE:
<221> NAME/KEY: PEPTIDE
<222> LOCATION: (31)..(31)
<223> OTHER INFORMATION: Phe-NH2

<400> SEQUENCE: 2

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Xaa
            20                  25                  30

<210> SEQ ID NO 3
<211> LENGTH: 31
<212> TYPE: PRT
<213> ORGANISM: rat
<220> FEATURE:
<221> NAME/KEY: PEPTIDE
<222> LOCATION: (31)..(31)
<223> OTHER INFORMATION: Phe-NH2

<400> SEQUENCE: 3

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 4
<211> LENGTH: 15
<212> TYPE: PRT
<213> ORGANISM: human
<220> FEATURE:
<221> NAME/KEY: PEPTIDE
<222> LOCATION: (15)..(15)
<223> OTHER INFORMATION: Phe-NH2

```
<400> SEQUENCE: 4

Pro Ala Trp Tyr Ala Ser Arg Gly Ile Arg Pro Val Gly Arg Xaa
1               5                   10                  15

<210> SEQ ID NO 5
<211> LENGTH: 20
<212> TYPE: PRT
<213> ORGANISM: human
<220> FEATURE:
<221> NAME/KEY: PEPTIDE
<222> LOCATION: (20)..(20)
<223> OTHER INFORMATION: Phe-NH2

<400> SEQUENCE: 5

Thr Pro Asp Ile Asn Pro Ala Trp Tyr Ala Ser Arg Gly Ile Arg Pro
1               5                   10                  15

Val Gly Arg Xaa
            20

<210> SEQ ID NO 6
<211> LENGTH: 15
<212> TYPE: PRT
<213> ORGANISM: human
<220> FEATURE:
<221> NAME/KEY: PEPTIDE
<222> LOCATION: (1)..(1)
<223> OTHER INFORMATION: Ac-Pro
<221> NAME/KEY: PEPTIDE
<222> LOCATION: (4)..(4)
<223> OTHER INFORMATION: Tyr(Ac)
<221> NAME/KEY: PEPTIDE
<222> LOCATION: (15)..(15)
<223> OTHER INFORMATION: Phe-NH2

<400> SEQUENCE: 6

Xaa Ala Trp Xaa Ala Ser Arg Gly Ile Arg Pro Val Gly Arg Xaa
1               5                   10                  15

<210> SEQ ID NO 7
<211> LENGTH: 15
<212> TYPE: PRT
<213> ORGANISM: human
<220> FEATURE:
<221> NAME/KEY: PEPTIDE
<222> LOCATION: (15)..(15)
<223> OTHER INFORMATION: Phe-NH2

<400> SEQUENCE: 7

Cys Ala Trp Tyr Ala Ser Arg Gly Ile Arg Pro Val Gly Arg Xaa
1               5                   10                  15

<210> SEQ ID NO 8
<211> LENGTH: 33
<212> TYPE: PRT
<213> ORGANISM: bovine

<400> SEQUENCE: 8

Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Phe Gly
                20                  25                  30

Arg

<210> SEQ ID NO 9
<211> LENGTH: 31
```

```
<212> TYPE: PRT
<213> ORGANISM: human

<400> SEQUENCE: 9

Ser Arg Ala His Gln His Ser Met Glu Ile Arg Thr Pro Asp Ile Asn
1               5                   10                  15

Pro Ala Trp Tyr Ala Gly Arg Gly Ile Ala Pro Val Gly Arg Phe
            20                  25                  30

<210> SEQ ID NO 10
<211> LENGTH: 30
<212> TYPE: PRT
<213> ORGANISM: human
<220> FEATURE:
<221> NAME/KEY: PEPTIDE
<222> LOCATION: (30)..(30)
<223> OTHER INFORMATION: Phe-NH2

<400> SEQUENCE: 10

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Xaa
            20                  25                  30

<210> SEQ ID NO 11
<211> LENGTH: 14
<212> TYPE: PRT
<213> ORGANISM: human
<220> FEATURE:
<221> NAME/KEY: PEPTIDE
<222> LOCATION: (14)..(14)
<223> OTHER INFORMATION: Phe-NH2

<400> SEQUENCE: 11

Thr Pro Asp Ile Asn Pro Ala Trp Tyr Ala Ser Arg Gly Xaa
1               5                   10

<210> SEQ ID NO 12
<211> LENGTH: 20
<212> TYPE: PRT
<213> ORGANISM: bovine
<220> FEATURE:
<221> NAME/KEY: PEPTIDE
<222> LOCATION: (20)..(20)
<223> OTHER INFORMATION: Phe-NH2

<400> SEQUENCE: 12

Thr Pro Asp Ile Asn Pro Ala Trp Tyr Ala Gly Arg Gly Ile Arg Pro
1               5                   10                  15

Val Gly Arg Xaa
            20

<210> SEQ ID NO 13
<211> LENGTH: 20
<212> TYPE: PRT
<213> ORGANISM: rat
<220> FEATURE:
<221> NAME/KEY: PEPTIDE
<222> LOCATION: (20)..(20)
<223> OTHER INFORMATION: Phe-NH2

<400> SEQUENCE: 13

Thr Pro Asp Ile Asn Pro Ala Trp Tyr Thr Gly Arg Gly Ile Arg Pro
1               5                   10                  15
```

```
-continued

Val Gly Arg Xaa
            20
```